(12) United States Patent
Menchen et al.

(10) Patent No.: US 7,928,038 B2
(45) Date of Patent: Apr. 19, 2011

(54) INTERMEDIATES AND METHODS FOR FORMING PASSIVATED SURFACES ON OXIDE LAYERS AND ARTICLES PRODUCED THEREBY

(75) Inventors: Steven M. Menchen, Fremont, CA (US); Christina E. Inman, San Mateo, CA (US); Meng Taing, Hayward, CA (US); Khai Luong, Oakland, CA (US); Handong Li, San Jose, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 518 days.

(21) Appl. No.: 11/943,851

(22) Filed: Nov. 21, 2007

(65) Prior Publication Data

US 2008/0176761 A1    Jul. 24, 2008

Related U.S. Application Data

(60) Provisional application No. 60/860,215, filed on Nov. 21, 2006, provisional application No. 60/860,480, filed on Nov. 22, 2006.

(51) Int. Cl.
*C40B 60/14* (2006.01)
*C12M 1/34* (2006.01)
*C07H 21/02* (2006.01)
*A61K 38/04* (2006.01)

(52) U.S. Cl. ...... 506/30; 435/288.3; 536/23.1; 530/326; 530/350

(58) Field of Classification Search ............... 506/30; 435/288.3; 536/23.1; 530/326, 350
See application file for complete search history.

(56) References Cited

U.S. PATENT DOCUMENTS

| | | | |
|---|---|---|---|
| 3,770,499 A | 11/1973 | Crowe et al. | |
| 6,093,370 A | 7/2000 | Yasuda et al. | |
| 6,146,767 A | 11/2000 | Schwartz | |
| 6,277,489 B1 | 8/2001 | Abbott | |
| 6,489,106 B1 | 12/2002 | Shivashankar et al. | |
| 6,645,644 B1 | 11/2003 | Schwartz et al. | |
| 6,811,980 B2 | 11/2004 | Ford | |

(Continued)

FOREIGN PATENT DOCUMENTS

CN    101568835    10/2009

(Continued)

OTHER PUBLICATIONS

Tosatti et al., Self-Assembled Monolayers of Dodecyl and Hydroxydodecyl Phosphates on Both Smooth and Rough Titanium and Titanium Oxide Surfaces, Langmuir 2002, pp. 3537-3548.

(Continued)

*Primary Examiner* — Jezia Riley

(57) ABSTRACT

Intermediates and methods for forming passivated surfaces on oxide layers and articles produced thereby are described. Hydroxyl or hydroxide groups on the oxide surfaces are reacted with a metal reagent of the formula $Y(L-Pol)_m$, where Y is a transition metal, magnesium or aluminum, L is oxygen, sulfur, selenium or an amine, and "Pol" represents a passivating agent such as a polyethylene glycol, a hydrocarbon, or a fluorocarbon. The resulting modified surface can be further reacted with a passivating agent having a phosphate functional group or a polyvalent reagent comprising a passivating moiety and a plurality of functional groups that are reactive with or that form complexes with Y. The passivating agent can also include a functional group such as biotin to provide surfaces with a desired functionality. The passivated surfaces exhibit minimal binding to bio-molecules and can be used in single-molecule detection schemes.

18 Claims, 18 Drawing Sheets

U.S. PATENT DOCUMENTS

| | | |
|---|---|---|
| 6,884,628 B2 | 4/2005 | Hubbell |
| 7,087,387 B2 | 8/2006 | Gerdes et al. |
| 7,361,471 B2 | 4/2008 | Gerdes et al. |
| 7,462,452 B2 | 12/2008 | Williams et al. |
| 7,585,965 B2 | 9/2009 | Scharnweber et al. |
| 2001/0029017 A1 | 10/2001 | Yasuda et al. |
| 2002/0048771 A1 | 4/2002 | Yasuda et al. |
| 2002/0055119 A1 | 5/2002 | Yasuda et al. |
| 2002/0055146 A1 | 5/2002 | Shivashankar et al. |
| 2002/0090641 A1 | 7/2002 | Yasuda et al. |
| 2002/0132242 A1 | 9/2002 | Gerdes et al. |
| 2002/0172963 A1 | 11/2002 | Kelley et al. |
| 2003/0027328 A1 | 2/2003 | Cunningham et al. |
| 2003/0082658 A1 | 5/2003 | Mallet et al. |
| 2003/0148401 A1 | 8/2003 | Agrawal et al. |
| 2004/0029162 A1 | 2/2004 | Chaton et al. |
| 2004/0091925 A1 | 5/2004 | Gerdes et al. |
| 2005/0003396 A1 | 1/2005 | Ozkan et al. |
| 2005/0142296 A1 | 6/2005 | Lakshmi |
| 2005/0266475 A1 | 12/2005 | Chaton et al. |
| 2006/0035229 A1 | 2/2006 | Scharnweber et al. |
| 2006/0194008 A1* | 8/2006 | Schwartz et al. ............ 428/34.4 |
| 2006/0205007 A1 | 9/2006 | Zhang et al. |
| 2006/0246225 A1 | 11/2006 | Moritz et al. |
| 2007/0015223 A1 | 1/2007 | Sanuki et al. |
| 2007/0098892 A1 | 5/2007 | Chung et al. |
| 2007/0238679 A1 | 10/2007 | Rank |
| 2008/0020214 A1 | 1/2008 | Kawai et al. |
| 2008/0032301 A1 | 2/2008 | Rank et al. |
| 2008/0044830 A1 | 2/2008 | Tovar et al. |
| 2008/0132429 A1 | 6/2008 | Perov et al. |
| 2008/0153100 A1 | 6/2008 | Rank et al. |
| 2008/0274671 A1 | 11/2008 | O'Donoghue et al. |
| 2009/0011949 A1 | 1/2009 | Hogan et al. |
| 2009/0082225 A1 | 3/2009 | Gerdes et al. |
| 2009/0156426 A1 | 6/2009 | Schiestel et al. |
| 2009/0197777 A1 | 8/2009 | Chagovetz et al. |

FOREIGN PATENT DOCUMENTS

| | | |
|---|---|---|
| EP | 0730168 | 9/2003 |
| EP | 1034430 | 2/2006 |
| EP | 1637613 | 3/2006 |
| EP | 1192448 | 9/2006 |
| EP | 2011898 | 1/2009 |
| EP | 2138462 | 12/2009 |
| WO | WO-99/30159 | 6/1999 |
| WO | WO-99/54718 | 10/1999 |
| WO | WO-01/02839 | 1/2001 |
| WO | WO-01/50131 | 7/2001 |
| WO | WO-02/20873 | 3/2002 |
| WO | WO-03/076903 | 9/2003 |
| WO | WO-2004/011672 | 2/2004 |
| WO | WO-2004/023128 | 3/2004 |
| WO | WO-2005/103226 | 11/2005 |
| WO | WO-2006/068619 | 6/2006 |
| WO | 2008/033867 | 3/2008 |
| WO | WO-2008/043551 | 4/2008 |
| WO | WO-2008/063134 | 5/2008 |
| WO | WO-2008/064291 | 5/2008 |
| WO | WO-2009/004117 | 1/2009 |
| WO | WO-2009/129410 | 10/2009 |

OTHER PUBLICATIONS

Textor et al., Structural Chemistry of Self-Assembled Monolayers of Octadecylphosphoric Acid on Tantalum Oxide Surfaces, Langmuir 2000, pp. 3257-3271.

Silverman et al., Comparative Properties of Siloxane vs Phosphonate Monolayers on A Key Titanium Alloy, Langmuir 2005, pp. 225-228.

Span et al., Surface Modification of Indium Tin Oxide by Phenoxytin Complexes, Langmuir 2001, pp. 948-952.

Jon et al., Construction of Nonbiofouling Surfaces by Polymeric Self-Assembled Monolayers, Langmuir 2003, pp. 9989-9993.

Midwood et al., Easy and Efficient Bonding of Biomolecules to an Oxide Surface of Silicon, Langmuir 2004, pp. 5501-5505.

Hofer et al., Alkyl Phosphate Monolayers, Self-Assembled from Aqueous Solution onto Metal Oxide Surfaces, Langmuir 2001, pp. 4014-4020.

Hanson et al., Bonding Self-Assembled, Compact Organophosphonate Monolayers to the Native Oxide Surface of Silicon, JACS Articles 2003, pp. 16074-16080.

Gao et al., Order-Disorder Transitions in Self-Assembled Monolayers: A $^{13}C$ Solid-State NMR Study, Langmuir 1997, pp. 115-118.

Gao et al., Self-Assembled Monolayers of Alkylphosphonic Acids on Metal Oxides, Langmuir 1996, pp. 6429-6435.

Frey et al., Peptomer Aluminum Oxide Nanoparticle Conjugates as Systemic and Mucosal Vaccine Candidates: Synthesis and Characterization of a Conjugate Derived from the C4 Domain of HIV-$1_{MN}$ Gp120, Bioconjugate Chem. 1997, pp. 424-433.

Folkers et al., Self-Assembled Monolayers of Long-Chain Hydroxamic Acids on the Native Oxides of Metals, Langmuir 1995, pp. 813-824.

Danahy et al., Self-Assembled Monolayers of $\alpha,\omega$-Diphosphonic Acids on Ti Enable Complete or Spatially Controlled Surface Derivatization, Langmuir 2004, pp. 5333-5337.

Brovelli et al., Highly Oriented, Self-Assembled Alkanephosphate Monolayers on Tantalum(V) Oxide Surfaces, Langmuir 1999, pp. 4324-4327.

Database WPI, Week 200652, *Thomson Scientific*, 2006-506068; XP002492928; & JP 2006 177914—Abstract only, Jul. 6, 2010.

EP 07868821, Office Action mailed Feb. 17, 2010.

Filippov, A., et al., "New Coating Materials For Hydrocarbon Discrimination Using A Multisensor System And Gas Chromatography", *Theoretical and Experimental Chemistry*, vol. 41, No. 6, 2005, 389-394.

WO 08/064291, IPRP, May 26, 2009.

WO 08/064291, PCT ISR, Sep. 4, 2008.

WO 08/064291, Written Opinion, May 21, 2009.

Filippov, A et al., "Discrimination of the saturated vapours of alcohols by the responses of assembly of piezoquartz sensors covered with metal stearates and their complexes with octadecylamine", Semiconductor Physics, Quantum Electronics & Optoelectronics, vol. 9(2), pp. 87-91 (2006).

* cited by examiner $$Y(OR_6)_m + mPol\text{-}LH \longrightarrow Y(L\text{-}Pol)_m + mR_6\text{-}OH$$

Y = Ta, Ti, Nb, Zr, Al $R_6$ = $C_1$-$C_5$ hydrocarbon

L = oxygen, sulfur, selenium, amine

Pol = PEG, substituted PEG, hydrocarbon, substituted hydrocarbon, fluorocarbon, substituted fluorocarbon

FIG. 2

TaPEG550 then PEGpentahydroxyl after 4 hr in buffer 100 nM LIZ-dATP

TaPEG550 then PEGpentahydroxyl 100 nM LIZ-dATP

INTERMEDIATES AND METHODS FOR FORMING PASSIVATED SURFACES ON OXIDE LAYERS AND ARTICLES PRODUCED THEREBY

This application claims the benefit of Provisional U.S. Patent Application Ser. No. 60/860,215, filed on Nov. 21, 2006, and Provisional U.S. Patent Application Ser. No. 60/860,480, filed on Nov. 22, 2006. Each of the above applications is incorporated by reference herein in its entirety.

The section headings used herein are for organizational purposes only and should not be construed as limiting the subject matter described herein in any way.

BACKGROUND

1. Technical Field

This application relates generally to surface modification techniques and, in particular, to intermediates and methods for forming passivated surfaces on oxide layers and to articles produced thereby.

2. Background of the Technology

DNA sequencing in real time requires the interrogation of individual incorporation events by polymerases, preferably on surfaces. Generally, these incorporation events are identified by examination of labels on the incorporated nucleotides as individual molecules (i.e., single molecule detection). The most popular labels are fluorescent dyes. Even rare non-specific adsorption of labeled nucleotides on the surfaces creates false positive signals. Therefore, binding of the substrates to the surfaces should be minimized.

There still exists a need for improved passivation techniques which would allow for the formation of thin passivation layers and which would result in surfaces exhibiting minimal absorption of biomolecules.

SUMMARY

According to a first embodiment, a method of modifying a surface of a support is provided which comprises:

contacting the surface with a metal reagent, wherein the surface comprises hydroxyl and/or oxide anion groups; and allowing the metal reagent to react with hydroxyl and/or oxide anion groups on the surface to form a modified surface;

wherein the metal reagent has a structure represented by the formula:

$Y(L\text{-Pol})_m$ wherein:
Y is a transition metal, magnesium or aluminum;
L is oxygen, sulfur, selenium or an amine;
each "Pol" group independently represents a polyethylene glycol, a substituted polyethylene glycol, a hydrocarbon, a substituted hydrocarbon, a fluorocarbon or a substituted fluorocarbon; and
m is an integer.

The method according to this embodiment can further comprise contacting the modified surface with a polyvalent reagent comprising a passivating moiety and a plurality of functional groups that are reactive with Y or that form complexes with Y, wherein the passivating moiety is selected from the group consisting of a substituted polyethylene glycol, an unsubstituted polyethylene glycol, a hydrocarbon, a substituted hydrocarbon, a fluorocarbon and a substituted fluorocarbon.

According to a second embodiment, a compound is provided which is represented by the formula (I), formula (II), or formula (III) below:

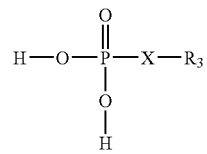
(I)

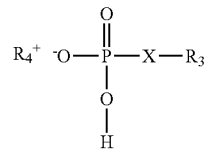
(II)

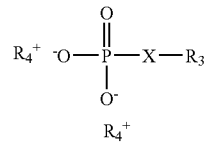
(III)

wherein:
X is O, N or a methylene group;
$R_3$ is polyethylene glycol, a substituted polyethylene glycol, a hydrocarbon, a substituted hydrocarbon, a fluorocarbon or a substituted fluorocarbon; and
$R_4$ is $N(R_2)_4$, or M, wherein M is Li, Na, K or Cs and wherein $R_2$ is an alkyl group.

According to a third embodiment, a compound is provided which comprises a metal complexing agent conjugated to a passivating agent, wherein:

the metal complexing agent is selected from the group consisting of a carboxylate, dopamine and anachelin; and wherein the passivating agent is selected from the group consisting of a polyethylene glycol, a substituted polyethylene glycol, a hydrocarbon, a substituted hydrocarbon, a fluorocarbon and a substituted fluorocarbon.

According to a fourth embodiment, a compound is provided which is represented by the formula:

$Y(L\text{-Pol})_m$ wherein:
Y is a transition metal, magnesium or aluminum,
L is oxygen, sulfur, selenium or an amine,
each "Pol" group independently represents a polyethylene glycol, a substituted polyethylene glycol, a hydrocarbon, a substituted hydrocarbon, a fluorocarbon or a substituted fluorocarbon, and
m is an integer.

According to a fifth embodiment, a method is provided which comprises:

reacting a first compound of the formula:

$Y(OR_6)_m$ with one or more second compounds each of the formula:

Pol-LH to form a metal ester compound of the formula $Y(L\text{-Pol})_m$ wherein:
Y is a transition metal, magnesium or aluminum, $R_6$ is a $C_1$-$C_5$ hydrocarbon, L is oxygen, sulfur, selenium or an amine, each "Pol" group independently represents a polyethylene glycol, a substituted polyethylene glycol, a hydrocarbon, a substituted hydrocarbon, a fluorocarbon or a substituted fluorocarbon, and m is an integer.

According to a sixth embodiment, a solid support is provided which comprises:

an oxide layer comprising an oxide of silicon, aluminum, germanium, gallium, indium, magnesium or tin; and moieties on a surface of the oxide layer, the moieties having a structure as set forth in formula (I) or formula (II) below:

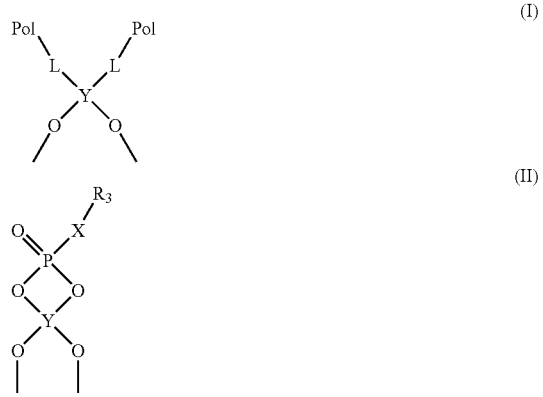

wherein:

X is O, N or a methylene group;

Y is a transition metal, magnesium or aluminum;

L is oxygen, sulfur, selenium or an amine or L is a metal complexing agent;

each "Pol" group independently represents a polyethylene glycol, a substituted polyethylene glycol, a hydrocarbon, a substituted hydrocarbon, a fluorocarbon or a substituted fluorocarbon; and $R_3$ is polyethylene glycol, a substituted polyethylene glycol, a hydrocarbon, a substituted hydrocarbon, a fluorocarbon or a substituted fluorocarbon; and wherein the oxygen atoms are bonded to the same or to different silicon, aluminum, germanium, gallium, indium or tin atoms in the oxide layer.

Non-limiting examples of the metal complexing agent include carboxylate, dopamine and anachelin.

According to a seventh embodiment, a solid support is provided which comprises:

an oxide layer comprising an oxide of silicon, aluminum, germanium, gallium, indium, magnesium or tin;

atoms of a metal selected from the group consisting of a transition metal, magnesium and aluminum bonded to the oxide layer; and a passivating reagent comprising a passivating moiety selected from the group consisting of a substituted polyethylene glycol, an unsubstituted polyethylene glycol, a hydrocarbon, a substituted hydrocarbon, a fluorocarbon and a substituted fluorocarbon;

wherein the passivating reagent is covalently bonded to or forms a complex with one or more atoms of the metal at a plurality of locations.

BRIEF DESCRIPTION OF THE DRAWINGS

The skilled artisan will understand that the drawings, described below, are for illustration purposes only. The drawings are not intended to limit the scope of the present teachings in any way.

FIG. 2 shows the preparation of a metal reagent which can be used to modify oxide surfaces.

DETAILED DESCRIPTION

The use of "or" herein means "and/or" unless stated otherwise or where the use of "and/or" is clearly inappropriate. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of." It should also be understood that in some embodiments the order of steps or order for performing certain actions is immaterial so long as the present teachings remain operable. Moreover, in some embodiments two or more steps or actions can be conducted simultaneously.

A technique for forming very thin layers of aluminum or transition metal compounds (e.g., esters) onto oxide (e.g., silica) surfaces, with the object of creating a passivated surface or creating a modified surface for reaction with a functional group on the end of a passivating agent, is provided. The passivating agent can be polyethylene glycol (i.e, PEG), which does not self assemble. The functional group can be a phosphate or a diphosphate group with a tetrabutyl ammonium counter ion, to make the reagent compatible for use in organic solvents.

Transition metal esters of Ta(5+), Ti(4+), and Zr(4+) are commercially available (e.g., as methyl, ethyl, and isopropyl esters). However, the reactivity of these esters with trace amounts of water to produce insoluble oxides precludes their use in an aqueous environment for coating surfaces. In addition, their limited solubility in organic solvents, especially the commercially available esters of Ti(4+), precludes the use of these reagents in many organic solvents.

The present inventors have found that the commercial esters of Ta(5+) and Ti(4+) can be reacted with four or more equivalents of medium molecular weight (i.e., 2 or more EO units) PEG mono-methyl ether to create a reagent with excellent solubility in most organic solvents, and with the capability of forming very thin layers of those metals on oxide surfaces such as silica surfaces, in a very predictable manner. In some cases, the deposition creates a passivated surface that is suitable for use in single-molecule detection schemes. In other cases, the modified surface can be further reacted with a phosphate or diphosphate derivative of PEG or another passivating agent to create a desired surface.

The overall scheme is summarized in FIGS. 1-5.

Figure 1A:
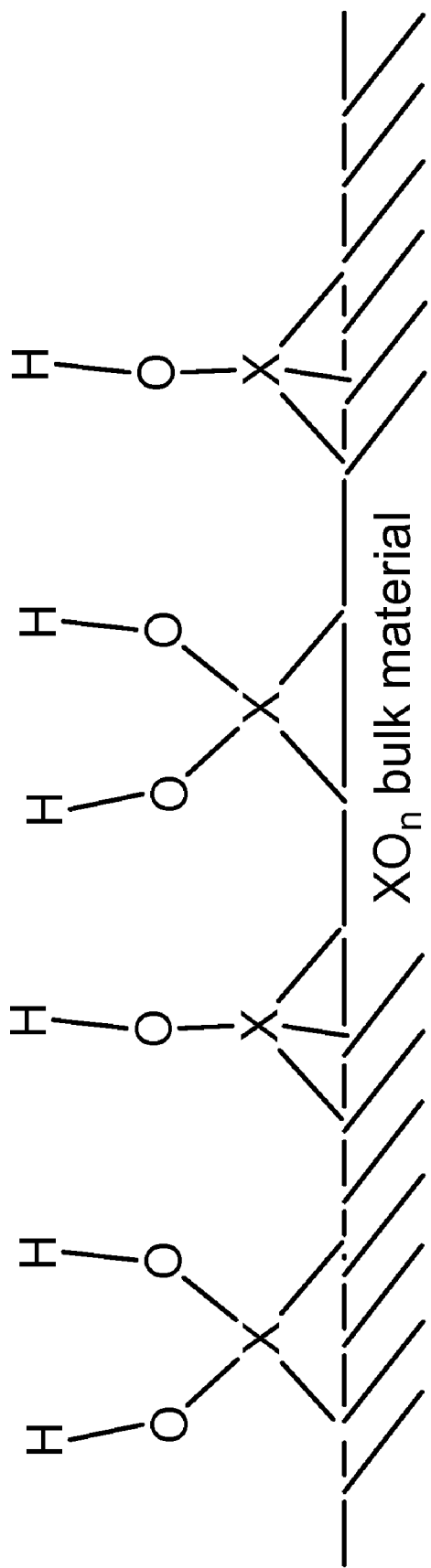
FIG. 1A is a schematic depicting an oxide surface comprising hydroxyl groups which can be passivated according to one embodiment.
Figure 1B:
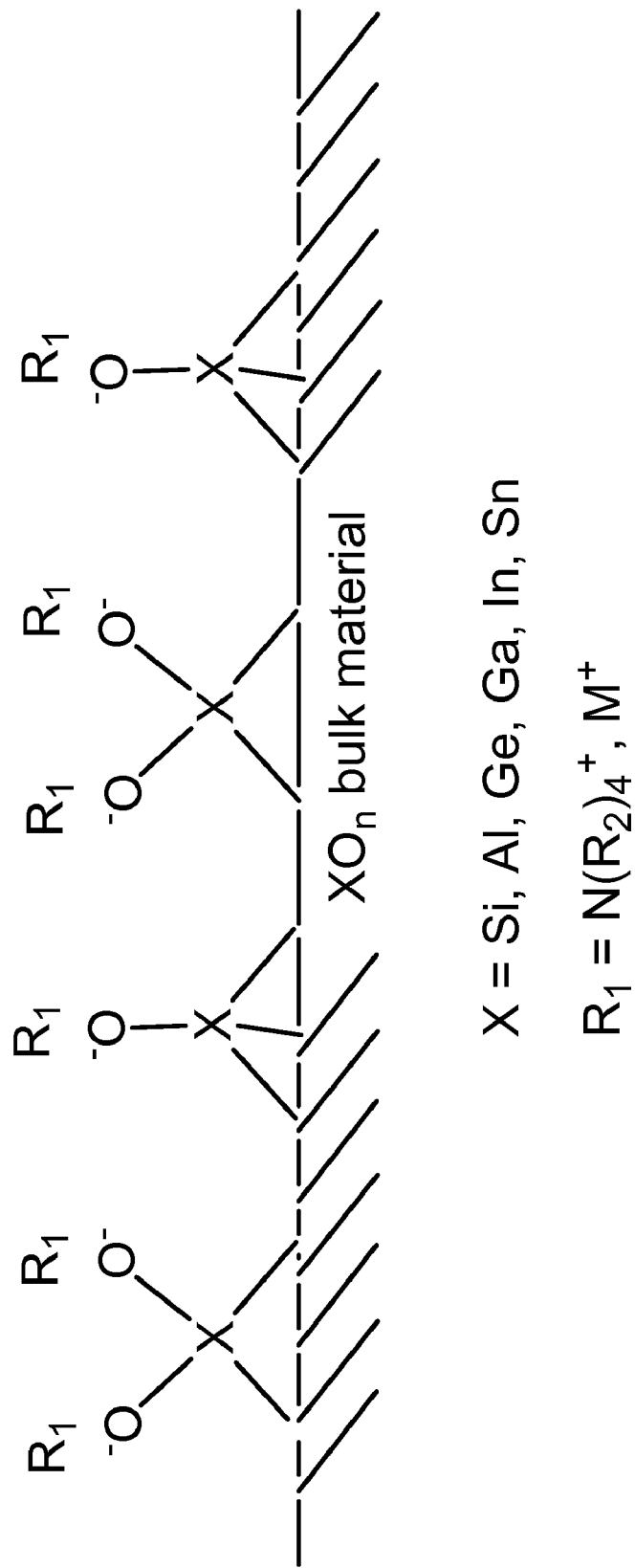
FIG. 1B is a schematic depicting surfaces comprising hydroxide anion groups which can be passivated according to a further embodiment.

FIG. 1A is a schematic depiction of the surface of an oxide material (e.g., silicate glass or quartz) which contains reactive hydroxyl groups. Hydroxyl groups on the surface can be converted to hydroxide anions by treatment with a base. FIG. 1B is a schematic depiction of the surface of an oxide material (e.g., silicate glass or quartz) which contains reactive hydroxide anion groups. According to one embodiment, hydroxyl groups on the surface can be converted to hydroxide anions by treatment with tetrabutylammonium hydroxide. This results in the formation of the quaternary ammonium salt which can be very easily solvated in organic media.

The oxide surface can be treated prior to passivation with an oxygen plasma or with tetrabutylammonium hydroxide, potassium hydroxide in methanol, hydrogen peroxide in sulfuric acid (i.e., "piranha" solution), nitric acid in sulfuric acid (i.e., "aquaregia"), hydrogen peroxide in ammonia (i.e., "RCA" solution), sulfuric acid, hydrofluoric acid, EDTA, or successive combinations of these treatments.

FIG. 2 illustrates the preparation of a metal reagent which can be used to modify oxide surfaces. In order to synthesize the reagent, more than the number of required equivalents (i.e., m) of the Pol-LH compound can be added to get total replacement of the low molecular weight alcohols on the metal. The PEG should be dry prior to addition to the metal ester. After several hours, the solution can be evacuated to remove displaced low molecular weight alcohol which aids in driving the reaction to completion.

Figure 3:
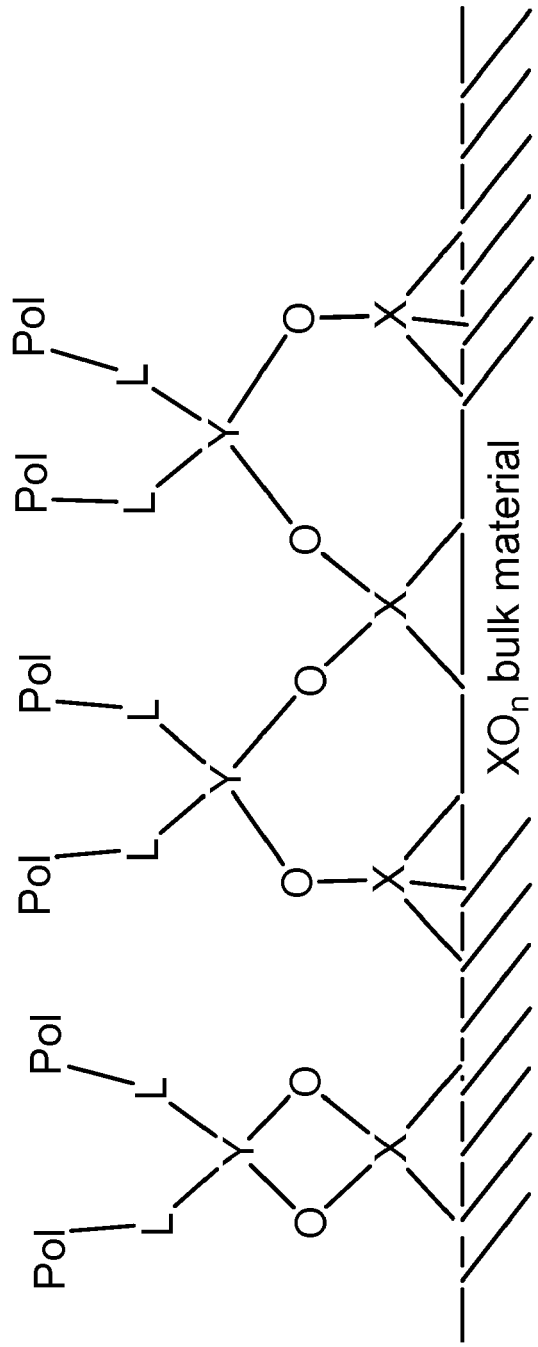
FIG. 3 shows a modified surface resulting from the reaction of a metal reagent compound with the oxide surface.

FIG. 3 shows the result of the reaction of the metal reagent with the oxide surface. In principle, residual "Pol" (e.g., PEG) groups are left on the un-reacted sites of the metal-ester, which are used later for conversion to the insoluble metal-partner pair. The presence of these "Pol" groups enables the use of a variety of solvents (e.g., ethyl acetate, toluene, methylene chloride, as examples) to take advantage of differing polarities, and refluxing temperatures, if either is required to optimize the speed of the deposition. It has been found that modification of the surface with the metal reagent results in a very thin layer (as demonstrated by elemental analysis at the surface by XPS) under a variety of conditions.

In some cases, the treatment of the oxide surface with the metal reagent yields the passivated surface. In other cases, the modified surface formed by treatment with the metal reagent is an intermediate to the formation of a passivated surface with an additional passivating step. FIG. 4A shows the chemical structure of a polymeric passivating agent with a complexing agent such as a phosphate or phosphonate which can be used to treat metal-reagent modified oxide surfaces to form passivated surfaces. In FIG. 4A, the substituent $R_3$ can be polyethylene glycol, a substituted polyethylene glycol, a hydrocarbon, a substituted hydrocarbon, a fluorocarbon or a substituted fluorocarbon.

Figure 4C:
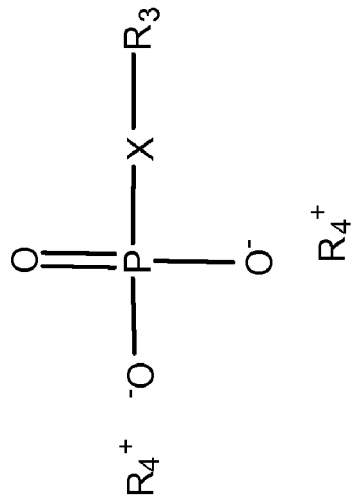
FIGS. 4A, 4B and 4C illustrate the chemical structures of passivating agents containing phosphate groups which can be reacted with surfaces treated with a metal reagent to form passivated surfaces.
Figure 4B:
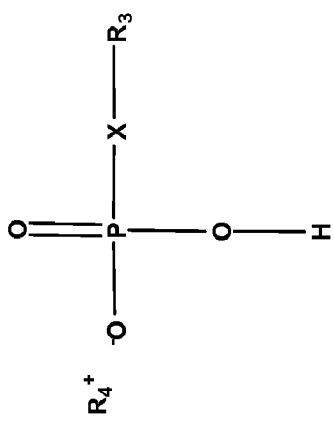
Figure 4A:
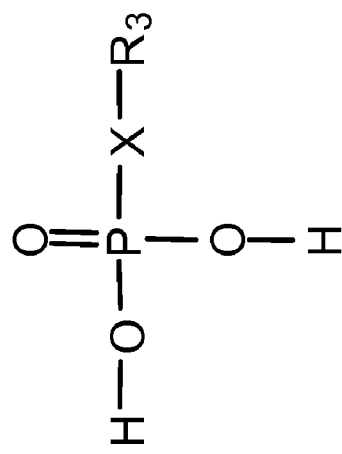

As indicated in FIGS. 4B and 4C, the phosphate esters can be converted to their salts (e.g., tetrabutylammonium salts) to improve solubility in a variety of organic solvents. In FIGS. 4B and 4C, the substituent $R_4$ can be $N(R_2)_4$ or M wherein $R_2$ is an alkyl group and M is Li, Na, K or Cs and the substituent $R_3$ can be polyethylene glycol, a substituted polyethylene glycol, a hydrocarbon, a substituted hydrocarbon, a fluorocarbon or a substituted fluorocarbon.

In addition, the polymeric passivating agent can contain substitutions to provide all or part of the surface with a desired functionality. For example, the $R_3$ substituent of the phosphate ester shown in FIGS. 4A-4C may include biotin moieties. In addition, the metal reagent treated surface can be contacted with a composition comprising a mixture of passivating agents having different polymeric elements to provide a surface optimized for a particular end-use application. For example, the passivating formulation may contain a mixture of PEG phosphates or diphosphates with fluorocarbon phosphates or diphosphates in order to obtain desired surface properties. The desired surface properties can be determined empirically, through experimentation. In FIGS. 4A-4C, X can be O, N or a methylene group and the $R_3$ substituent can be polyethylene glycol, a substituted polyethylene glycol, a hydrocarbon, a substituted hydrocarbon, a fluorocarbon or a substituted fluorocarbon. Also in FIGS. 4B and 4C, each $R_4$ substituent can be $N(R_2)_4$, or M, wherein M is Li, Na, K or Cs and wherein $R_2$ is an alkyl group.

Figure 5:
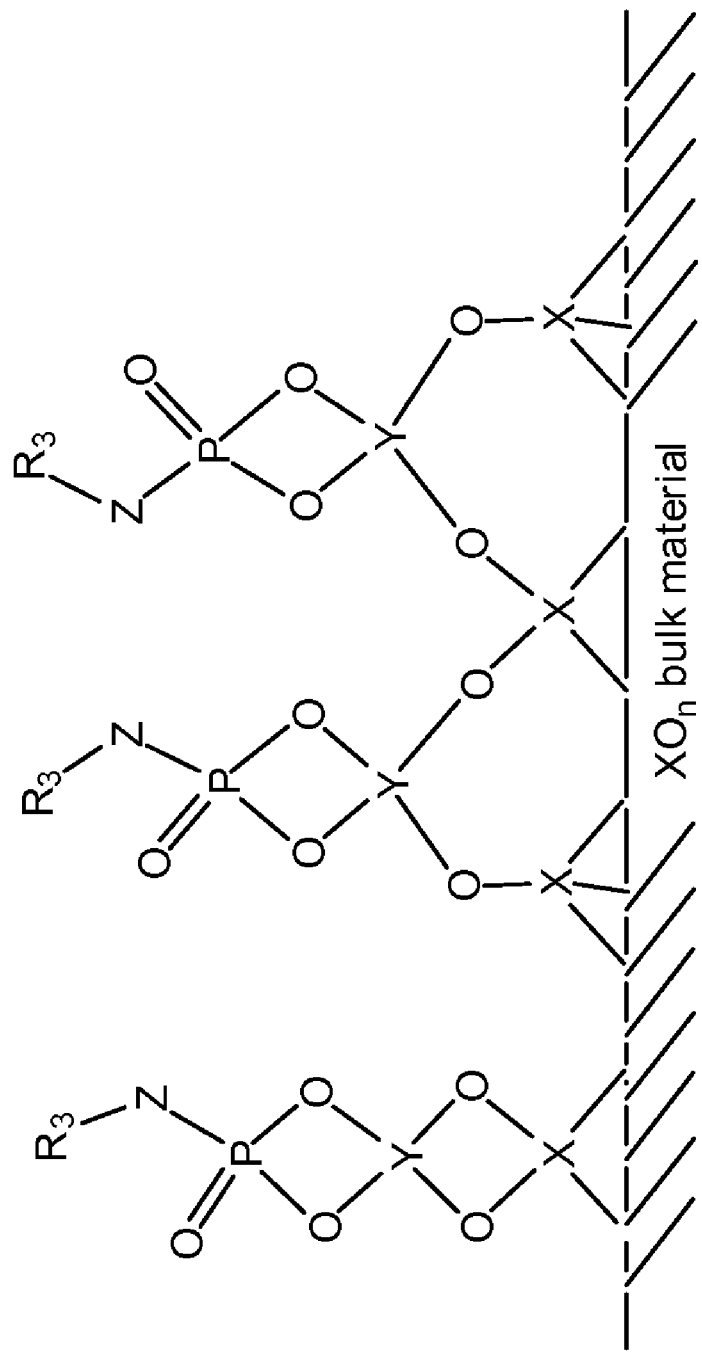
FIG. 5 is a schematic showing the result of the interaction of a metal reagent treated surface with a passivating agent comprising a phosphate group.

FIG. 5 shows a surface formed by treating an oxide surface with a passivating agent comprising a phosphate group wherein the oxide surface has been previously treated with a metal reagent. As can be seen from FIG. 5, this technique results in a thin-layer of the passivating agent on the oxide surface. In FIG. 5, the $R_3$ substituent can be polyethylene glycol, a substituted polyethylene glycol, a hydrocarbon, a substituted hydrocarbon, a fluorocarbon or a substituted fluorocarbon. Also in FIG. 5, Y can be a transition metal, magnesium or aluminum and Z can be O, N or a methylene group.

The use of the metal reagents described herein enables controlled formation of very thin layers of metal precursor on a variety of oxide surfaces. In addition, the surfaces can be formed under very mild conditions. The metal reagents are also easy to make and require no purification prior to use.

The use of a metal reagent pre-layer and a phosphate functional passivating agent enables the use of readily available phosphate functionality for the deposition of the desired surface. The phosphates can be readily synthesized from phosphorous oxychloride and the alcohol versions of the passivating agents. The synthesized phosphates can be converted to derivatives (e.g., quaternary ammonium derivatives) that are readily soluble in a variety of solvents, and that still maintain their reactivity with the metal reagent modified surfaces. Reaction of the phosphate with the surface does not require extensive heating or self-assembly of the tailed phosphates on the surface.

Figure 6:
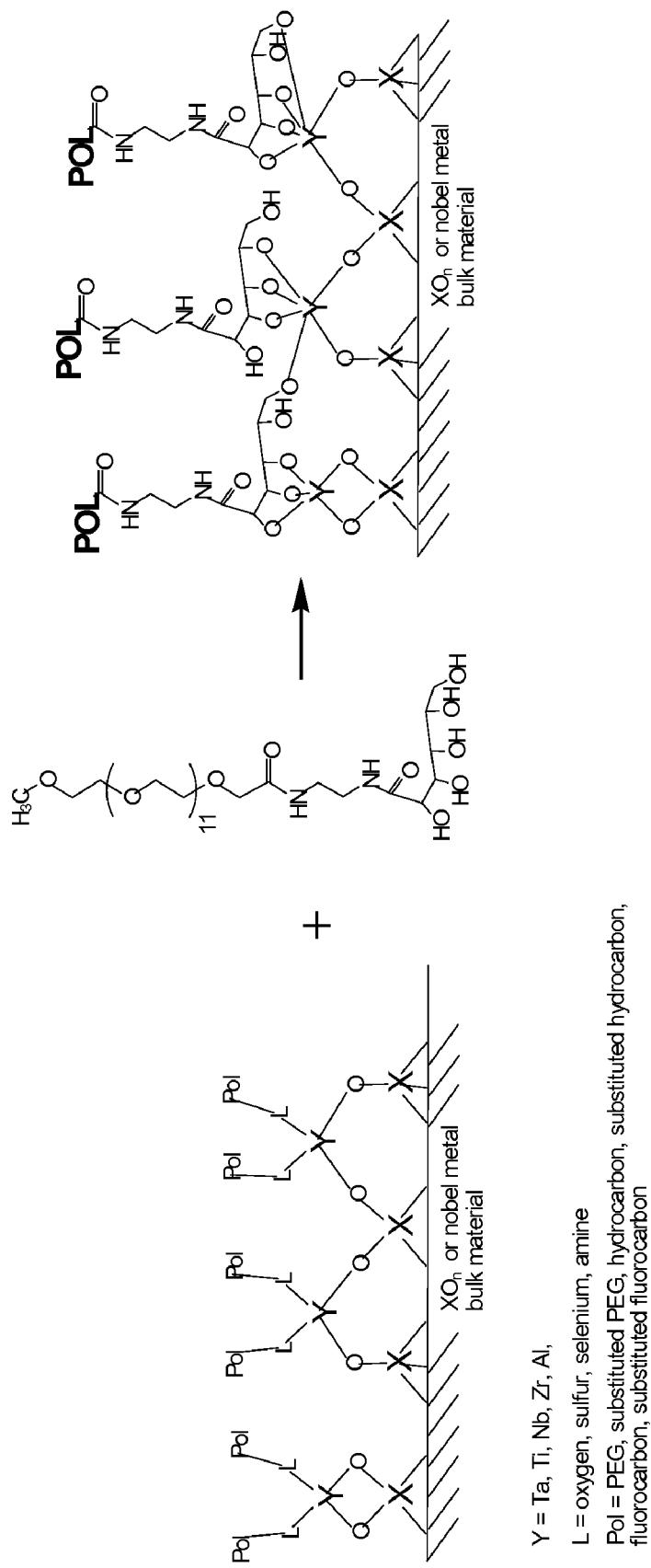
FIG. 6 illustrates the displacement of a labile monovalent passivating agent on a surface with a multivalent PEG passivating agent comprising a plurality of hydroxyl groups.

The use of metal reagents and phosphate functional passivating agents also enables the creation of a variety of surface types and properties by formulating phosphate esters with different polymeric groups. For example, phosphates of hydrocarbon, fluorocarbon, and PEG alcohols could be mixed together prior to contact with the metal-reagent treated oxide surface to obtain a modified surface with desirable properties for a specific application. In addition, a phosphate ester containing a specific functionality (e.g., biotin) could be used to obtain a surface that would bind another molecule (e.g., streptavidin).

groups capable of forming covalent bonds or forming complexes with metal atoms on the surface. For example, the multivalent passivating agent can displace the monovalent passivating agent on the transition metal oxide surface while maintaining the transition metal layer between the oxide surface and the passivating agent. A schematic depiction of the displacement of the monovalent passivating agent with a multivalent passivating agent is illustrated in FIG. 6. In this manner, the multivalent passivating agent can impart substantial hydrolytic stability to the passivated surface.

The passivating moiety on the multivalent passivating agent can be a moiety selected from the group consisting of: a substituted polyethylene glycol; an unsubstituted polyethylene glycol; a hydrocarbon; a substituted hydrocarbon; a fluorocarbon and a substituted fluorocarbon.

The plurality of functional groups that are reactive with the metal atoms on the surface or that form complexes with the metal atoms on the surface can be hydroxyl groups, amine groups, phosphate groups, phosphonate groups, thiol groups, alkylphosphate groups, carboxyl groups or combinations thereof.

A general formula for a multivalent passivating agent is shown below.

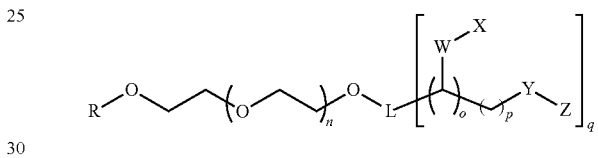

wherein: R is H, alkyl, aryl or a functional group; L is a linker group or a covalent bond; each W and Y are independently O, NH, S or phosphonate; each X and Z are independently H, phosphate, alkylcarboxy or alkylphosphate; n is 3 to 100; o is 1-8; p is 0-8; and q is 1-3. As shown in the above formula, the multivalent passivating agent comprises a unsubstituted polyethylene glycol as the passivating moiety. Although an unsubstituted polyethylene glycol passivating moiety is depicted, other passivating moieties as described above can also be employed.

A method of synthesizing a multivalent passivating agent comprising a polyethylene glycol passivating moiety and a plurality of hydroxyl functional groups is shown below.

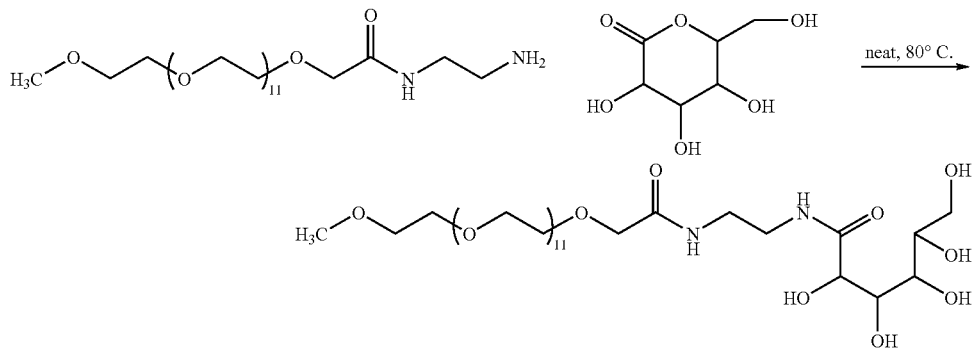

Treatment of Metal Reagent Modified Surfaces with a Multivalent Passivating Agent According to some embodiments, the surface of a support treated with a metal reagent as described above can be subsequently treated with a multivalent passivating agent comprising a passivating moiety and a plurality of functional As shown in the above reaction scheme, an amino-functional compound comprising a polyethylene glycol moiety can be reacted with 3,4,5-trihydroxy-6-(hydroxymethyl)tetrahydro-2H-pyran-2-one at 80° C. to form the multivalent passivating agent. For this multivalent passivating agent, the variables in the general formula above are defined as follows: R is methyl;

n is 11, s is 1, q is 1, M is C=O, N is —NH—C—C—NH—(C=O)—, o is 4, W and Y are O, X and Z are H, and p is 1.

As set forth above, the linker L in the above formula can be a linker group. Exemplary linker groups include, but are not limited to, a group represented by the formula: —(C)$_s$—(C=O)-Q-R'-Q-(C=O)— wherein each Q is independently —O— or —NH—, R' is an aliphatic or aromatic group and s is an integer of 0 to 10.

An exemplary polyvalent reagent corresponding to the above general formula is represented by the following formula:

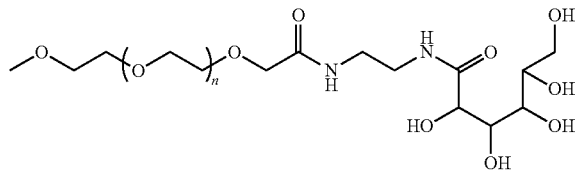

wherein n is a positive integer. For example, n can be 3 to 100.

According to some embodiments, the polyvalent reagent can be represented by the following formula:

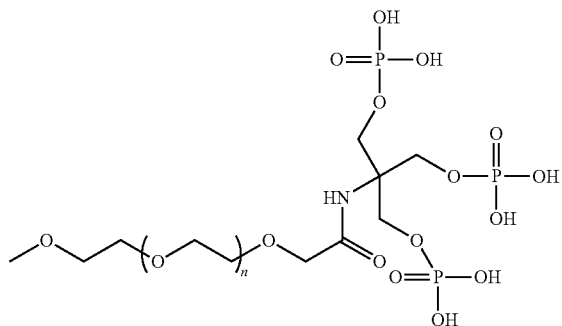

wherein n is a positive integer. For example, n can be 3 to 100.

A solid support having a surface treated with a multivalent passivating agent as set forth above is also provided. According to some embodiments, a solid support is provided which comprises: an oxide layer comprising an oxide of silicon, aluminum, germanium, gallium, indium, magnesium or tin; atoms of a metal selected from the group consisting of a transition metal, magnesium and aluminum bonded to the oxide layer; and a passivating reagent comprising a passivating moiety selected from the group consisting of a substituted polyethylene glycol, an unsubstituted polyethylene glycol, a hydrocarbon, a substituted hydrocarbon, a fluorocarbon and a substituted fluorocarbon; wherein the passivating reagent is covalently bonded to or forms a complex with one or more atoms of the metal at a plurality of locations.

As set forth above, modification of a surface with metal esters enables very controlled, very thin layer deposition of a metal precursor to a variety of oxide surfaces under very mild conditions. The metal esters are very easy to make, and require no purification prior to use. The use of a combination of metal ester deposition followed by multivalent passivating agent deposition can enable the creation of a variety of surfaces types and properties. For example, the surface can be treated with a multivalent passivating agent having different functional groups during the final surface modification.

Synthesis of Multivalent Passivating Agents Comprising Phosphate Moieties

The multivalent passivating agent can be readily synthesized using known chemical synthesis techniques. An exemplary synthesis technique is described above for a multivalent passivating agent comprising polyethylene glycol as a passivating moiety and a plurality of hydroxyl functional groups capable of bonding to metal atoms on a support surface. A method for synthesizing a multivalent passivating agent comprising a polyethylene glycol passivating moiety and a plurality of phosphate moieties is described below. The phosphate moieties are capable of forming complexes with metal atoms on a support surface.

Synthesis and Purification of Methyl PEG$_{2000}$-Acetic Acid

A first step of the method comprises the synthesis of a Methyl PEG$_{2000}$-Acetic Acid intermediate. This intermediate can be synthesized by the procedure set forth below.

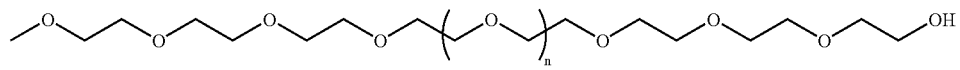

Average Molecular Weight 2000: 2012 plus/minus (44)n

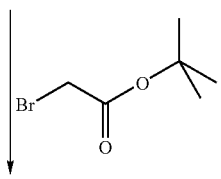

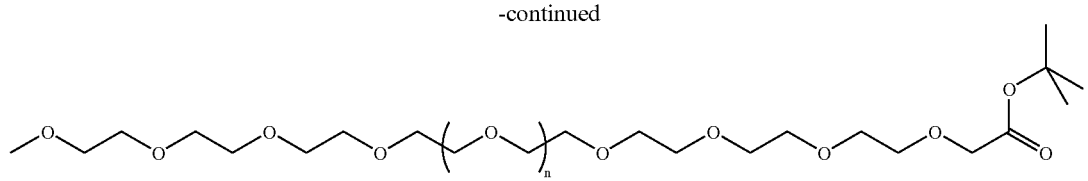

Average Molecular Weight 2000: 2026 plus/minus (44)n

↓ HCl, pH 1.0

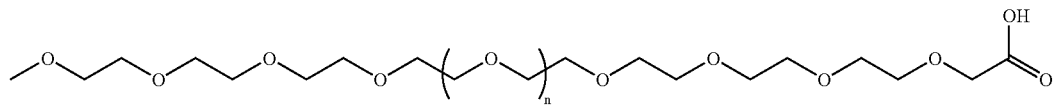

Average Molecular Weight 2000: 2070 plus/minus (44)n

This procedure is described below.

1) Methyl-PEG$_{2000}$ alcohol (100 gram, av. 0.05 mole) was dissolved in 100 ml anhydrous dichloromethane (DCM) with NaOH (6 g, 0.15 moles) added and chilled on ice under nitrogen.

2) Bromoacetic t-butyl ester (30 g, 0.15 moles) was added portionwise with stirring. The final mixture was agitated (stirring became difficult due to formation of NaBr solid) at room temperature for 24 hours.

3) The NaBr precipitate was removed by centrifugation or decanting. Remove most of DCM on a rotavap. Add hexane to extract out unreacted Bromoacetic t-butyl ester. The semisolid after decanting hexane was adjusted to pH 1.0 with HCl (conc.) on ice and stirred overnight at room temperature.

4) The product was extracted with DCM three times (total 500 ml), washed with brine, and dried with anhydrous NaSO$_4$. Remove most of the DCM on a Rotavap. Add to cold hexane dropwise with stirring to precipitate the product.

5) A white solid product (85 grams) was collected, washed with hexane, dried under vacuum, and characterized by mass spectrometry (MS) both positive and negative mode with Matrix Assisted Laser Desorption Ionization (MALDI). The yield was 83%.

Synthesis and Column Purification of mPEG2K Acetamido-Tris-Alcohol

The Methyl PEG2K-Acetic Acid intermediate reaction product can then be reacted with 2-amino-2-(hydroxymethyl) propane-1,3-diol as set forth below to form a second intermediate comprising a plurality of hydroxyl groups (i.e., an mPEG2K Acetamido-Tris-Alcohol).

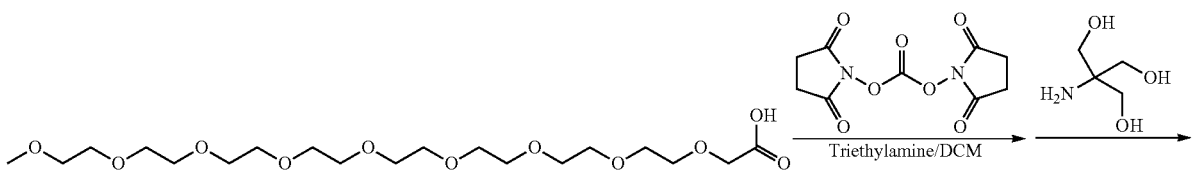

Average Molecular weight 2000: 2070 plus/minus (44)n

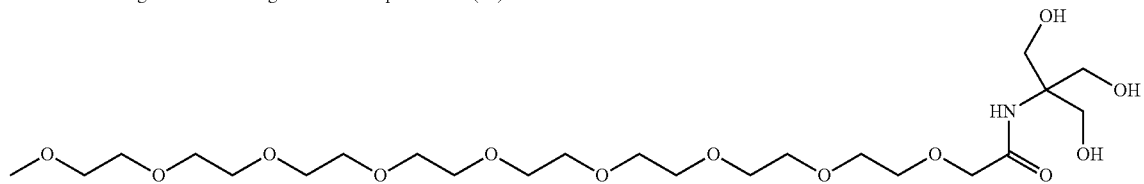

Average Molecular weight 2000: 2173 plus/minus (44)n

This procedure is described below.

1) Methyl PEG$_{2000}$-acetic acid (12 gram, av. 0.006 mole) was co-evaporated with anhydrous toluene and acetonitrile, respectively three times (30 ml each) and redissolved in dry dichloromethane (10 ml). Triethylamine (TEA) (0.75 ml, 0.006 mole) was added under dry nitrogen. Disuccinimidyl carbonate (DSC) (3 gram, 0.012 moles) was added portionwise under nitrogen with stirring. The reaction was left at room temperature for 4 hours and the solvent was removed on a rotavap. Anhydrous dioxane (10 ml) was added to dissolve the residue, and the solution added dropwise to a saturated trishydroxymethylaminomethane (Tris base) aqueous solution with vigorous stirring. The reaction was left for two hours at room temperature and then extracted with DCM (total 100 ml) three times. The DCM phase was dried with sodium sulfate and an oil crude was obtained after removal of solvent.

2) The residue was purified on a silica gel (100 ml) column packaged in 5% MeOH-DCM and eluted with 5% MeOH-DCM. Fraction 12-20 were identified as the desired product (9.5 gram) by MALDI-MS and proton nuclear magnetic resonance spectroscopy (HNMR). Yield was 76%.

3) $R_f$ value of the product was about 0.5 in 10% MeOH-DCM on a silica TLC plate.

Synthesis and Purification of Methyl PEG-2K Acetamido-Tris-Triphosphate

The mPEG$_{2000}$ Acetamido-Tris-Alcohol intermediate can then be reacted with bis(2-cyanoethyl)diisopropylphosphoramidite as set forth below to form the multivalent passivating agent.

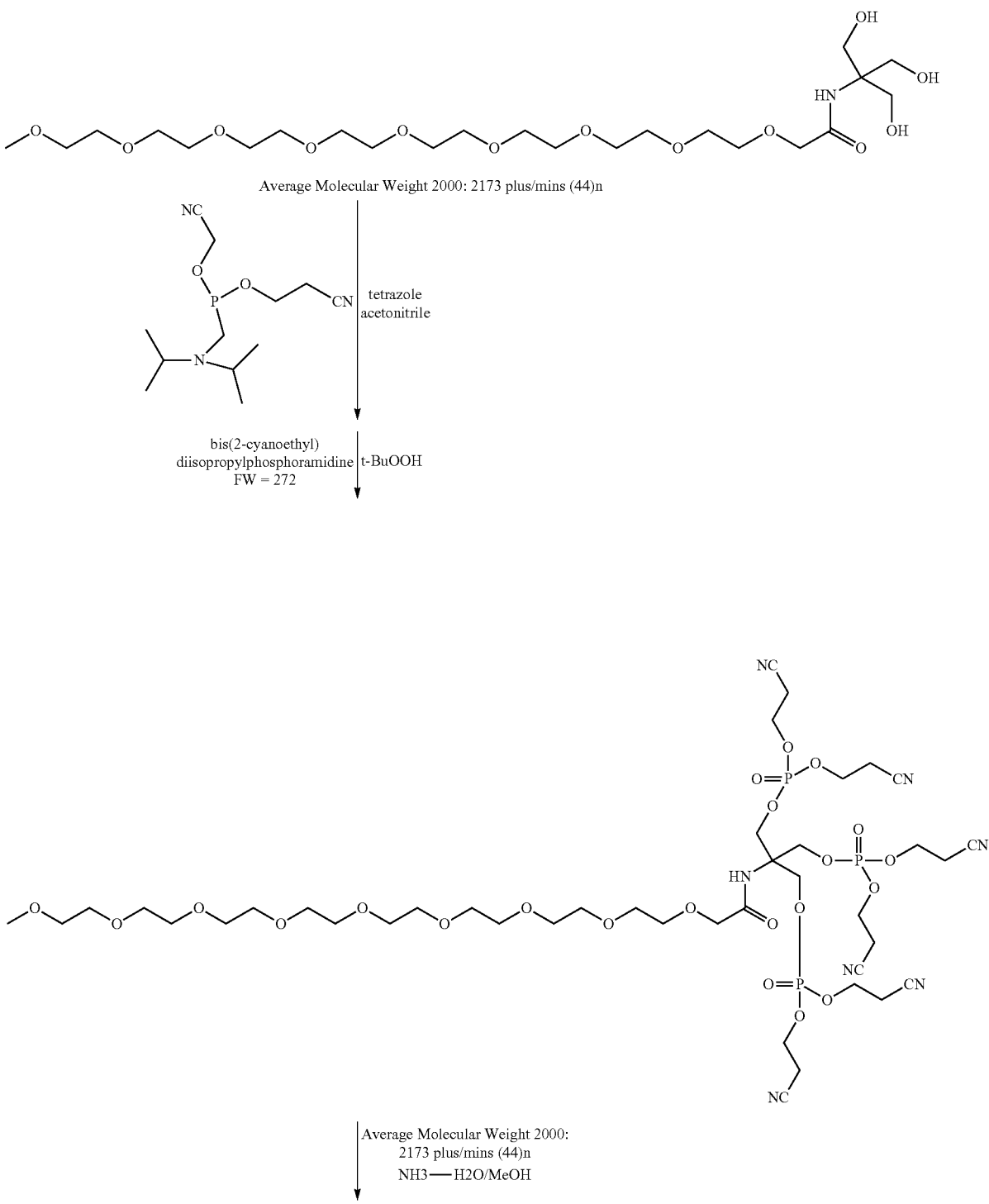

-continued

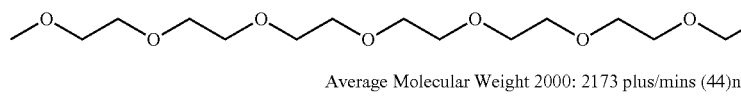
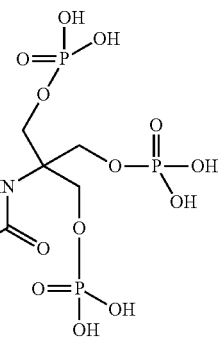

Average Molecular Weight 2000: 2173 plus/mins (44)n

This procedure is described below.

1) mPEG2K acetamido-Tris-alcohol (2.2 gram, 1 mmole) was coevaporated with anhydrous toluene and acetonitrile, respectively, three times (30 ml each). Bis(2-cyanoethyl) diisopropylphosphoramidite (FW=271.6, 1.22 g, 4.5 mmoles) and tetrazole-acetonitrile solution (15 ml, 0.45M, 6.75 mmoles) were added under nitrogen. The reaction mixture was stirred at room temperature for 3 hours. Tert-Butyl hydroperoxide (70% aqueous, 6 ml, 45 mmoles) was added and the mixture was stirred at room temperature for 2 hours. The solvent was removed on a rotavap. The residue was extracted with DCM three times and washed with sodium bicarbonate buffer (pH 9) and dried over sodium sulfate. The residue was silica gel column purified with eluent 10% methanol in DCM. Fractions 15-20 were identified as the desired product by MS and HNMR.

2) $R_f$ of the product was 0.55 in 10% MeOH-DCM on a silica TLC plate.

3) The purified phosphonate ester was placed in $NH_3.H_2O$ (5 ml) and incubated overnight at room temperature. The ammonia was removed under vacuum, re-dissolved in water and purified on Sephadex DEAE A-25 column (equilibrated with 2M potassium bicarbonate and washed thoroughly with water). The phosphate was eluted with 2M triethylamine acetate buffer. The buffer was removed by repeatedly co-evaporating with water under vacuum and the product (1.7 gram) was characterized by MALDI-MS, proton NMR and phosphor NMR. Yield was 70%.

Synthesis and Purification of Methyl PEG-350 Acetamido-Tris-Triphosphate

Using the starting material methyl PEG 350 alcohol with an average molecular weight 350, methyl PEG-350 acetamido-Tris-Triphosphate was synthesized following the same procedure for the synthesis of methyl PEG-2K acetamido-Tris-Triphosphate.

EXPERIMENTAL

Aspects of the present teachings may be further understood in light of the following examples, which should not be construed as limiting the scope of the present teachings in any way.

Surfaces Treated with Metal Reagents and TEG Phosphate

XPS data are shown in the table below for a tantalum PEG-ester modified silicon dioxide surface after performing the following manipulations on the surface:

treatment of the quartz cover-slip for 16 hr. at 77° C. temperature with a 15 mM solution of tantalum (5) that had been converted to its PEG 550 (monomethyl ether) ester by exchange of ethyl alkoxides with PEG 550 in ethyl acetate;

subsequent treatment with 20 mM tetra(n-butyl)ammonium salt of tetraethylene glycol (monomethyl) monophosphate (TEG phosphate) in toluene at 110° C. for 4 days.

| Element | Atomic % |
| --- | --- |
| Oxygen | 54.4 |
| Carbon | 25.3 |
| Tantalum | 2.2 |
| Silicon | 10.2 |
| Phosphorus | 7.6 |

XPS data are shown in the table below for a titanium PEG-ester modified silicon dioxide surface after performing the following manipulations on the surface:

treatment of the quartz cover-slip for 18 hr. at methylene dichloride reflux with a 0.0002 M solution of titanium (4) that had been converted to its PEG 550 (monomethyl ether) ester by exchange of ethyl alkoxides with PEG 550 in methylene dichloride solvent;

subsequent treatment of the 0.005 M tetra(n-butyl)ammonium salt of tetraethylene glycol (monomethyl) monophosphate in methylene dichloride solvent at methylene dichloride reflux for 24 hr.

| Element | Atomic % |
| --- | --- |
| Oxygen | 53.8 |
| Carbon | 24.4 |
| Titanium | 2.3 |
| Silicon | 15.8 |
| Phosphorus | 3.5 |

The absorption of bio-molecules to these modified surfaces was tested by measuring the fluorescence from the surface after incubating with fluorescent labeled bio-molecules.

Figure 7B:
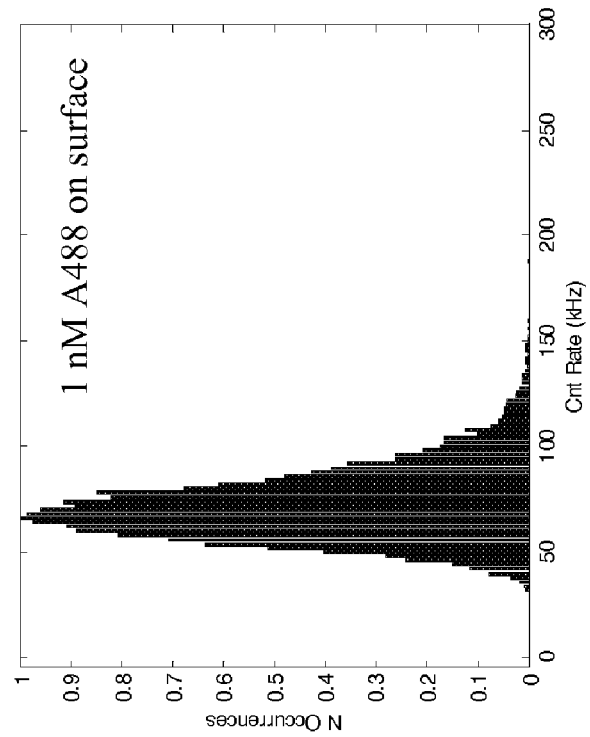
FIGS. 7A-7E are plots showing the results from confocal fluorescence imaging of coverslips with TaPEG$_{550}$/TEG phosphate modified surfaces wherein the plots are histograms of the count rates in the pixels of a 100×100 μm image.
Figure 7A:
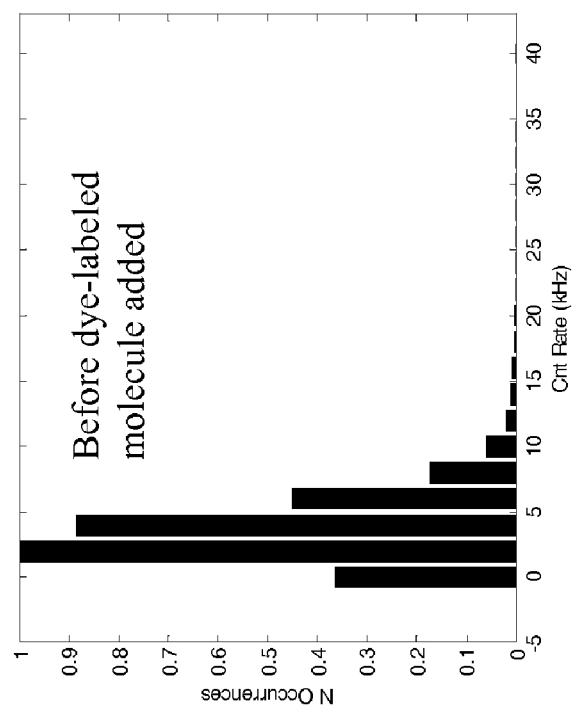
Figure 7C:
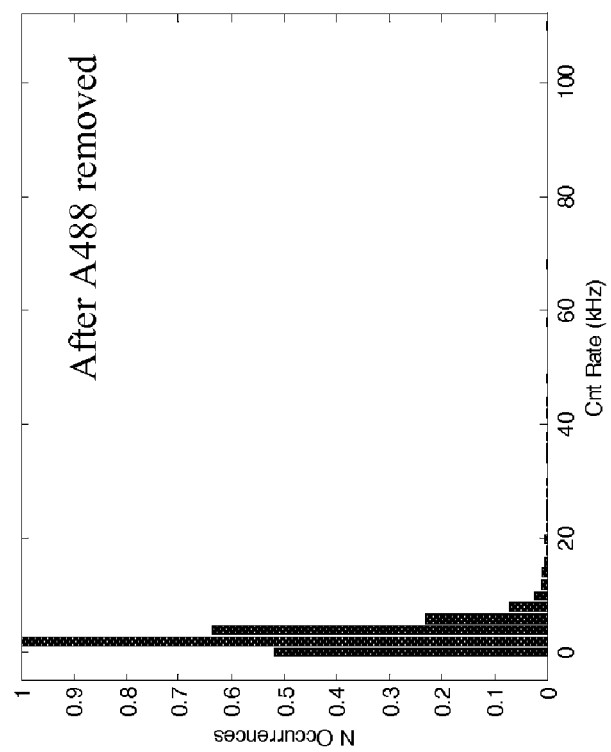
Figure 7D:
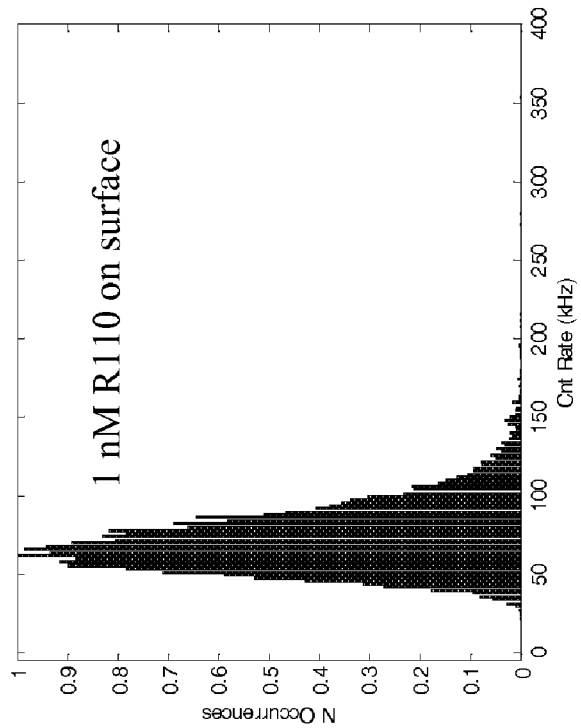
Figure 7E:
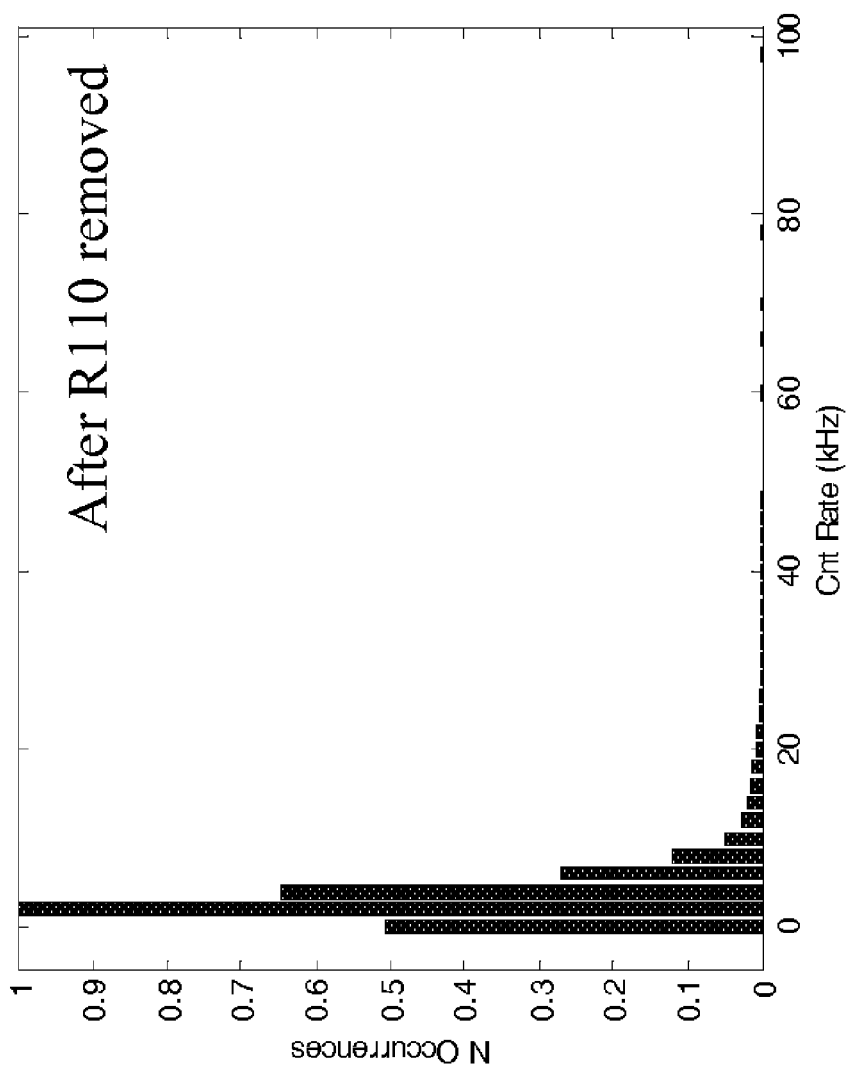

FIGS. 7A-7E are plots showing the results from confocal fluorescence imaging of coverslips with $TaPEG_{550}$/TEG phosphate modified surfaces. The plots are histograms of the count rates in the pixels of a 100×100 μm image. FIG. 7A shows that, before any dye is added, the background fluorescence signal peaks around 2.5 kHz. FIGS. 7B and 7C show that when a 1 nM A488 solution is added, the count rate histogram peak shifts to 70 kHz and drops again back to signal levels comparable to the background when the dye is removed. This is repeated with a 1 nM R110 solution in the same 100×100 μm region as shown in FIG. 7D. Again, the results show that the fluorescence signals return to background levels when R110 is removed from the coverslip (FIG.

7E). These results demonstrate that the rhodamine dyes A488 and R110 do not non-specifically bind to the modified surface.

Figure 8B:
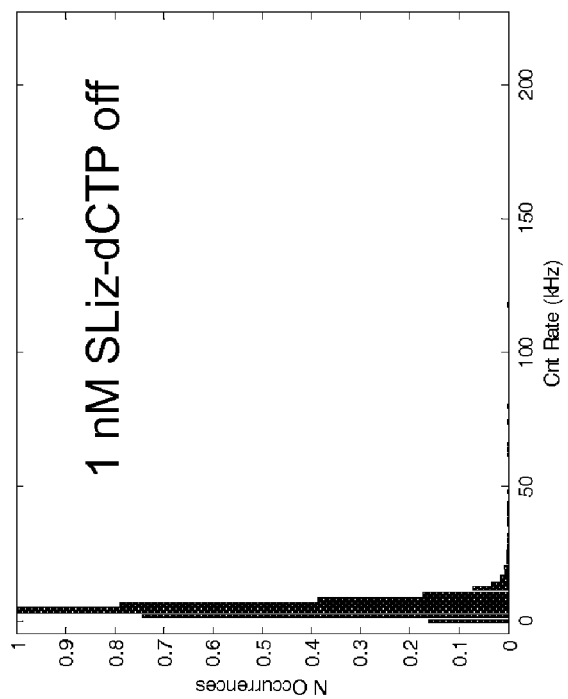
FIGS. 8A-8C are plots showing count rate histograms of a TaPEG$_{550}$ (no phosphate) modified surface using sulfo-Liz dCTP.
Figure 8A:
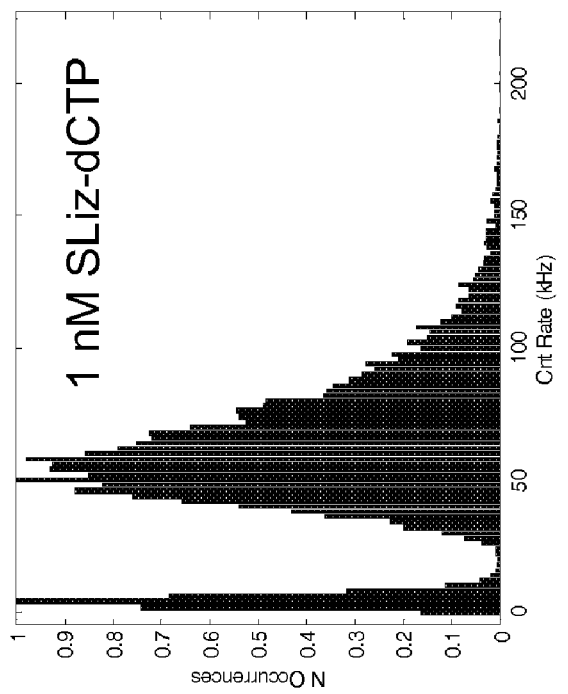
Figure 8C:
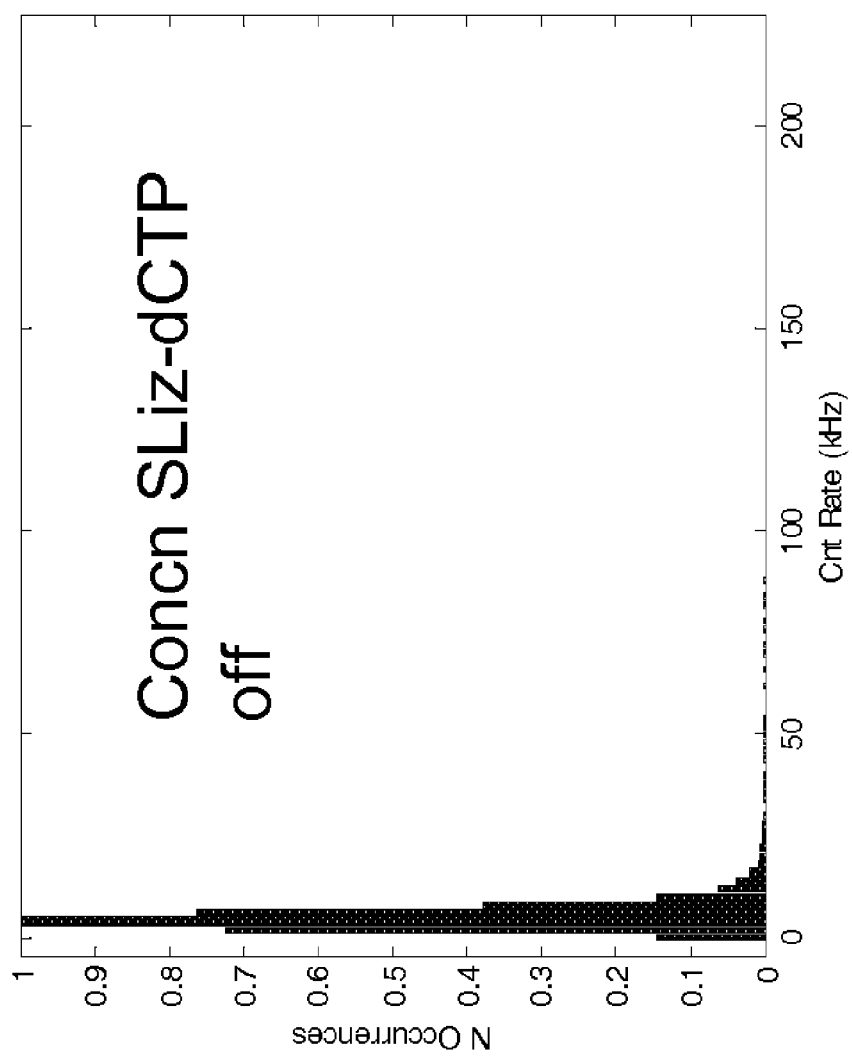

FIGS. 8A-8C are plots showing similar count rate histograms of a TaPEG$_{550}$ (no phosphate) modified surface using sulfo-Liz dCTP which demonstrate that the modified surface prevents sulfo-Liz dCTP from nonspecifically binding to the coverslip. This is observed even when a high concentration sulfo-Liz dCTP solution is added onto the surface (FIG. 8B) and removed (FIG. 8C). Again, these results demonstrate that sulfo-Liz dCTP does not non-specifically bind to the modified surface.

Figure 9A:
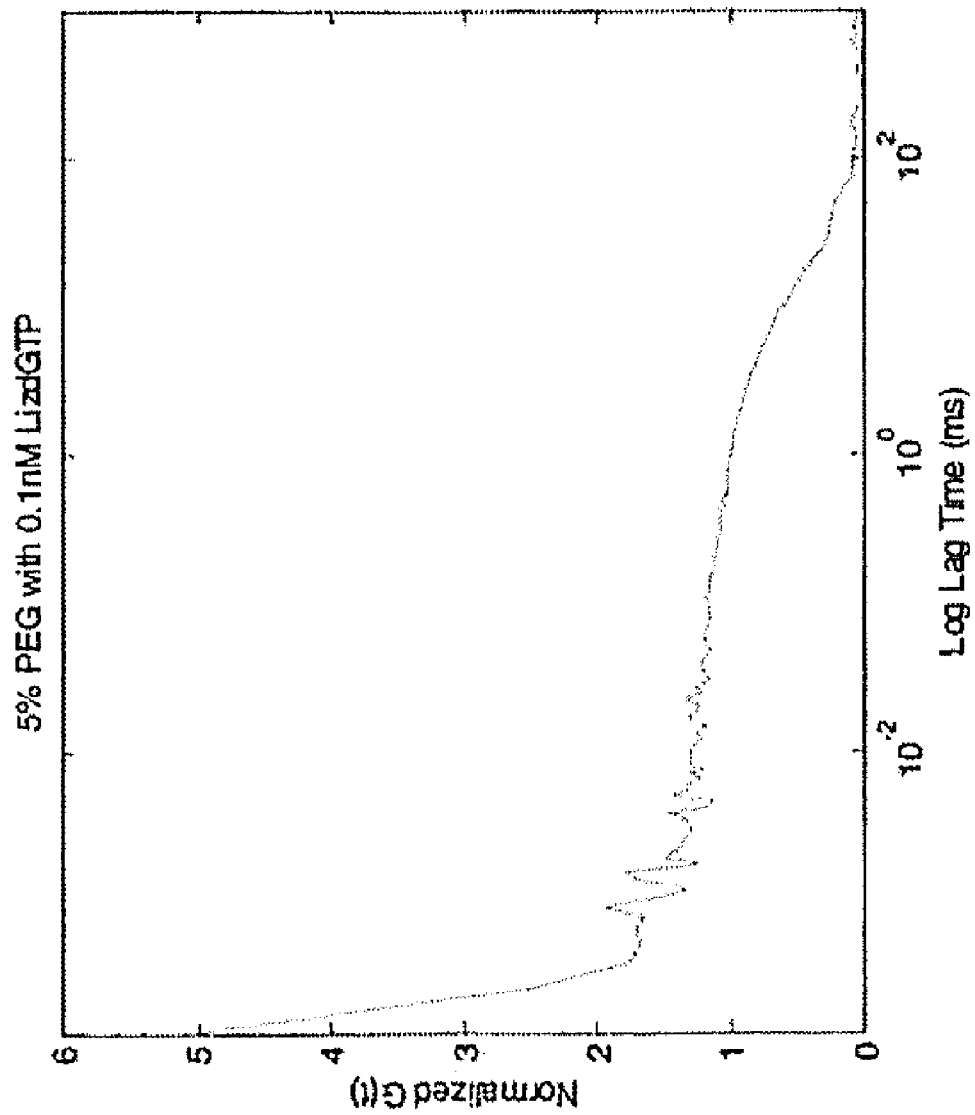
FIG. 9A is a correlation curve obtained from 0.1 nM Liz-dGTP on conventionally prepared 5% Pegsilane modified coverslips showing a tail at long lag times (e.g., 10 ms) indicative of sticky dyes at the surface.
Figure 9C:
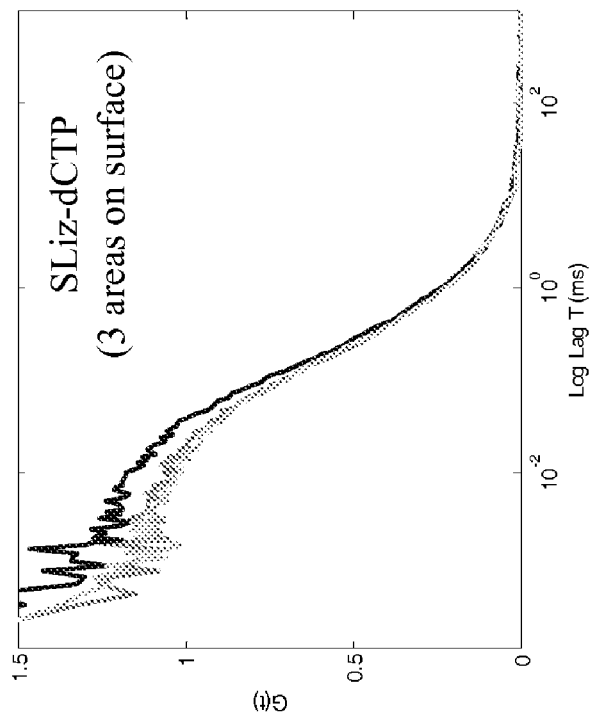
FIGS. 9B and 9C show the correlation curves obtained from fluorescence correlation spectroscopy (FCS) of dilute solutions of rhodamine dyes and sulfoLiz dCTP diffusing above a TaPEG$_{550}$ surface modified coverslip.
Figure 9B:
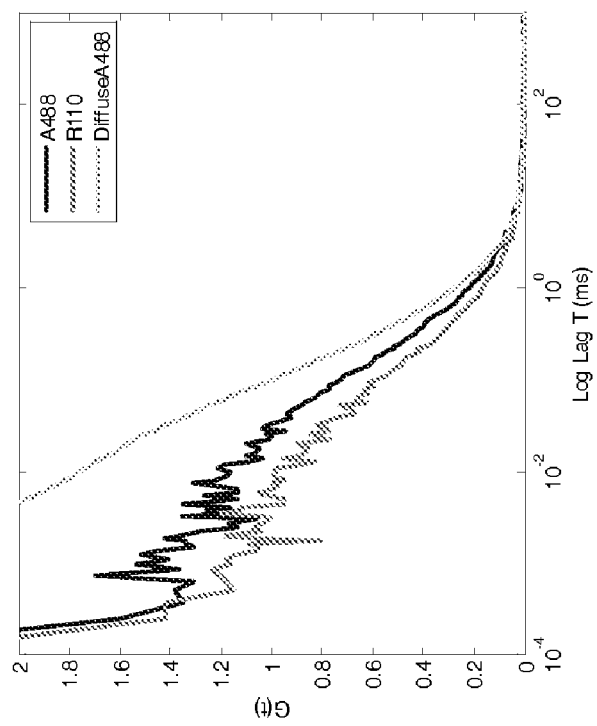

FIGS. 9A-9C illustrate a comparison of the correlation curves obtained from fluorescence correlation spectroscopy (FCS) of dilute solutions of the above rhodamine dyes and the sulfoLiz dCTP in contact with TaPEG$_{550}$ and silane PEG surface modified coverslips. The decay rate of the correlation curves provide information on the rate of diffusion of the free dyes in solution. Hence, if a dye sticks to the surface, the correlation curve will decay more slowly. For comparison, FIG. 9A is an example of a correlation curve exhibiting a tail at long lag times (e.g., 10 ms) indicative of sticky dyes at the surface. The data for FIG. 9A was obtained from 0.1 nM Liz-dGTP on conventionally prepared 5% PEGsilane modified coverslips wherein the PEGsilane was deposited from refluxing toluene.

FIG. 9B is a plot showing the correlation curves from dilute solutions of A488 and R110 diffusing above the modified surface. This plot also shows the correlation curve for freely diffusing A488 above a known non-sticky surface for comparison. FCS experiments were also done using dilute solutions of sulfo-Liz dCTP, the results of which are shown in FIG. 9C. This plot shows the results from three different FCS measurements at different positions on the modified coverslip. Together, these FCS results and the fluorescence imaging results above indicate that the TaPEG$_{550}$ modified surfaces on fused silica substrate do not non-specifically bind A488, R110, and sulfo-Liz dCTP.

Treatment of Metal Reagent Modified Surfaces with Multi-Valent Passivating Agents A quartz surface was treated with ethanolic Ta(monomethyl-PEG$_{550}$)$_5$ to form a modified surface. The modified surface was then treated with an ethanolic solution of a multivalent passivating agent having the following structure:

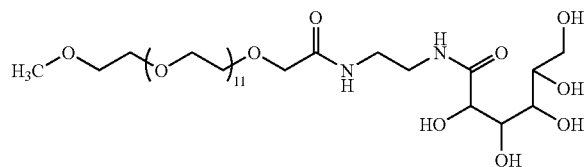

which is designated penta(hydroxyl)-monomethyl-PEG$_{550}$. The results are shown in FIGS. 10A-10D.

Figure 10A:
FIG. 10A shows non-specific binding data for 1 nm fluorescent LIZ dye solution on a quartz surface treated with Ta(monomethyl-PEG$_{550}$)$_5$ followed by treatment with an ethanolic solution of penta(hydroxyl)monomethyl-PEG$_{550}$.
Figure 10B:
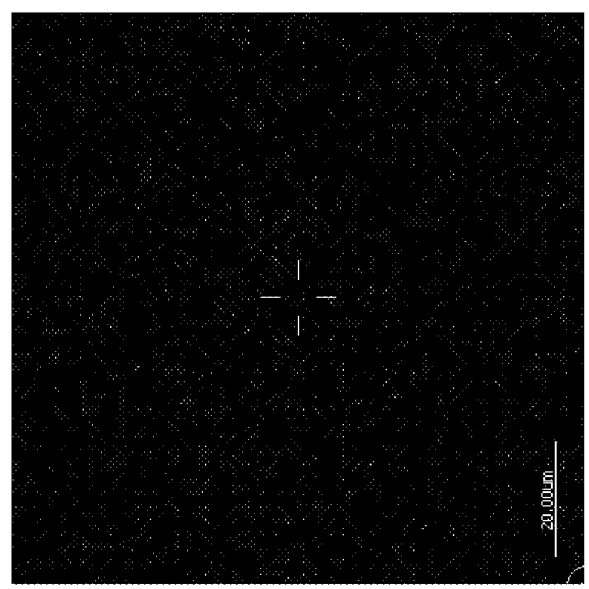
FIG. 10B shows non-specific binding data for a 1 nm fluorescent LIZ dye solution after 4 hours in the presence of the buffer on a quartz surface treated with Ta(monomethyl-PEG$_{550}$)$_5$ followed by treatment with an ethanolic solution of penta(hydroxyl)monomethyl-PEG$_{550}$.
Figure 10D:
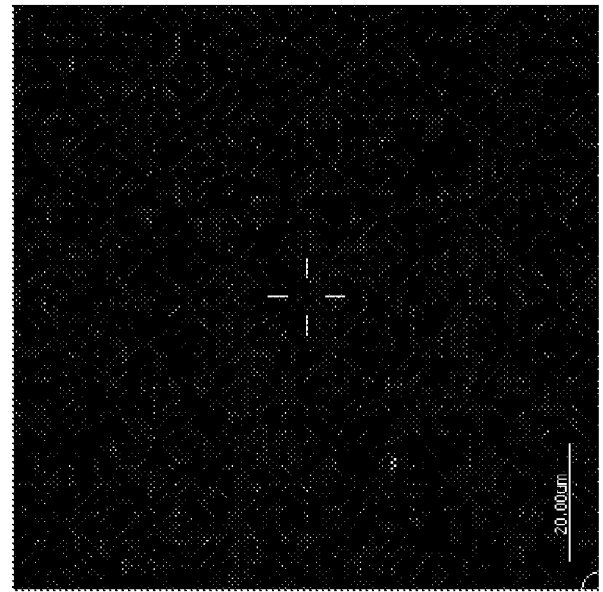
FIG. 10D shows non-specific binding data for a 100 nm fluorescent LIZ dye solution after 4 hours in the presence of the buffer on a quartz surface treated with Ta(monomethyl-PEG$_{550}$)$_5$ followed by treatment with an ethanolic solution of penta(hydroxyl)monomethyl-PEG$_{550}$.
Figure 10C:
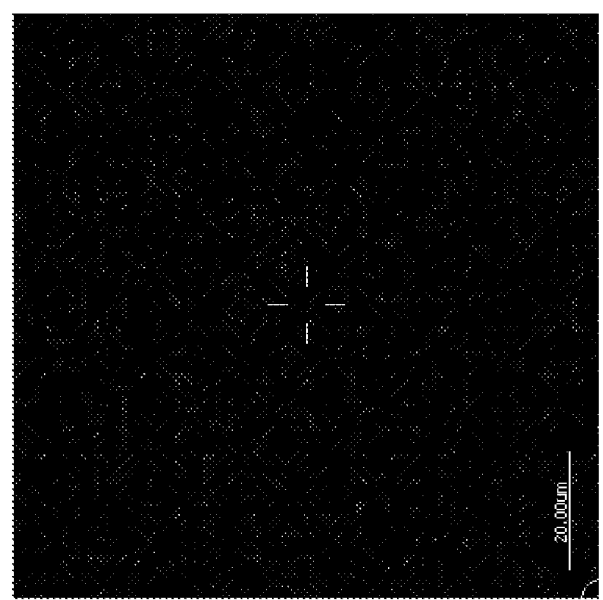
FIG. 10C shows non-specific binding data for 100 nm fluorescent LIZ dye solution on a quartz surface treated with Ta(monomethyl-PEG$_{550}$)$_5$ followed by treatment with an ethanolic solution of penta(hydroxyl)monomethyl-PEG$_{550}$.

FIG. 10A shows non-specific binding data for 1 nm fluorescent LIZ dye solution on a quartz surface treated with Ta(monomethyl-PEG$_{550}$)$_5$ followed by treatment with an ethanolic solution of penta(hydroxyl)monomethyl-PEG$_{550}$. FIG. 10B shows non-specific binding data for a 1 nm fluorescent LIZ dye solution treated with Ta(monomethyl-PEG$_{550}$)$_5$ followed by treatment with an ethanolic solution of penta(hydroxyl)monomethyl-PEG$_{550}$ after it had been incubated in a Tris buffer solution for 4 hours. FIG. 10C shows non-specific binding data for 100 nm fluorescent LIZ dye solution on a quartz surface treated with Ta(monomethyl-PEG$_{550}$)$_5$ followed by treatment with an ethanolic solution of penta(hydroxyl)monomethyl-PEG$_{550}$. FIG. 10D shows non-specific binding data for a 100 nm fluorescent LIZ dye solution on a quartz surface treated with Ta(monomethyl-PEG$_{550}$)$_5$ followed by treatment with an ethanolic solution of penta(hydroxyl)monomethyl-PEG$_{550}$ after the surface had been incubated in a Tris buffer solution for 4 hours. As can be seen from FIGS. 10A-10D, treatment with the multivalent passivating agent yields a surface that prevents non-specific adsorption of a 100 nM aqueous solution of Liz fluorescent dye even after 4 hours in the presence of a buffer.

Figures 11A, 11B, 11C:
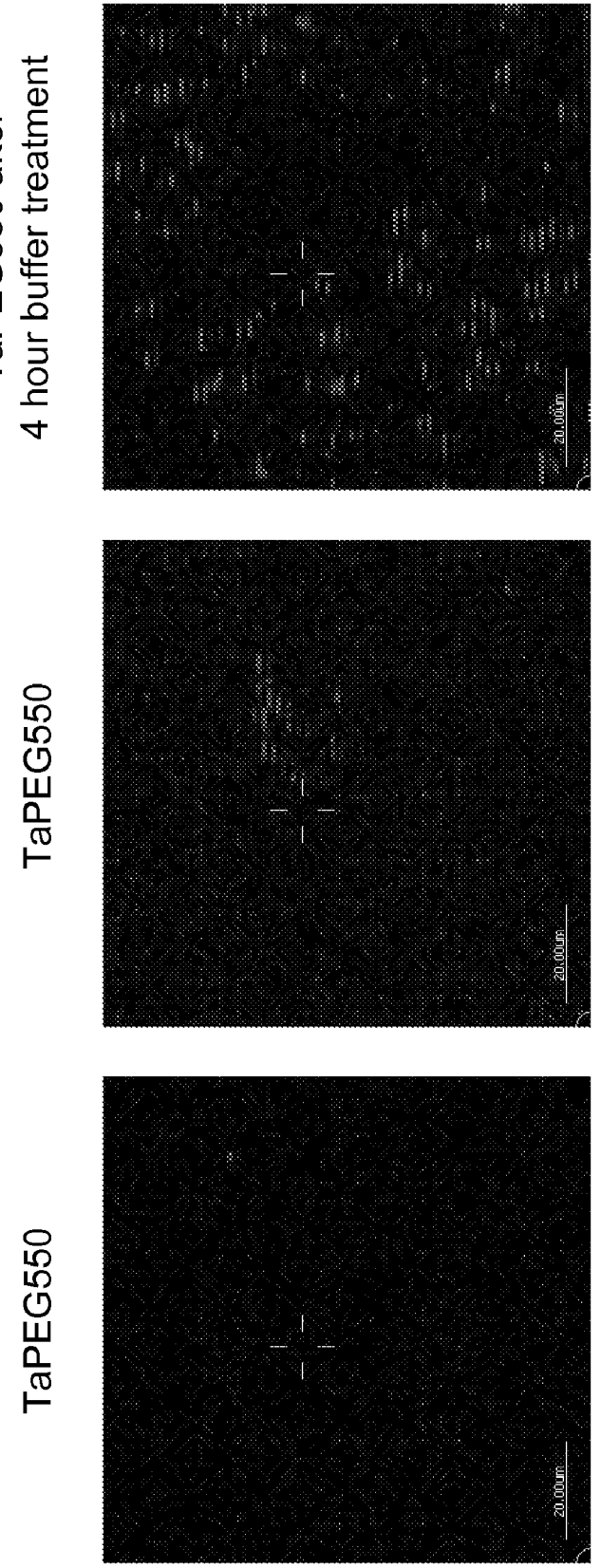
FIG. 11A shows non-specific binding data for 1 nM fluorescent LIZ dye solution on a quartz surface treated with Ta(monomethyl-PEG$_{550}$)$_5$.
FIG. 11B shows non-specific binding data for 100 nM fluorescent LIZ dye solution on a quartz surface treated with Ta(monomethyl-PEG$_{550}$)$_5$.
FIG. 11C shows non-specific binding data for 1 nM fluorescent LIZ dye solution after 4 hours in the presence of a buffer on a quartz surface treated with Ta(monomethyl-$PEG_{550}$)$_5$

In contrast, as shown in FIG. 11A-11C, some sticking of 1 nM of fluorescent Liz dye (FIG. 11A) and 100 nM of fluorescent Liz dye (FIG. 11B) was observed on Ta(monomethyl-PEG$_{550}$)$_5$ treated quartz slides which were not treated with the multivalent passivating agent. Extensive sticking was observed after 4 hours in the presence of a buffer (FIG. 11C).

The integrity of the Ta surface after treatment with the multivalent passivating agent (i.e., poly(hydroxyl)-monomethyl-PEG) is demonstrated by XPS of the modified quartz surfaces before and after poly(hydroxyl)-monomethyl-PEG modification, shown below.

| XPS Data For Surface Treated With TaPEG$_{550}$ Reagent | |
|---|---|
| Element | Percentage |
| Oxygen | 63.19 |
| Carbon | 9.43 |
| Tantalum | 0.66 |
| Silicon | 26.71 |

| XPS Data For Surface Treated With TaPEG$_{550}$ Reagent Followed By Poly(Hydroxyl)-Monomethyl-PEG | |
|---|---|
| Element | Percentage |
| Oxygen | 52.3 |
| Nitrogen | 2.5 |
| Carbon | 26.8 |
| Tantalum | 0.43 |
| Silicon | 18.0 |

Figure 12B:
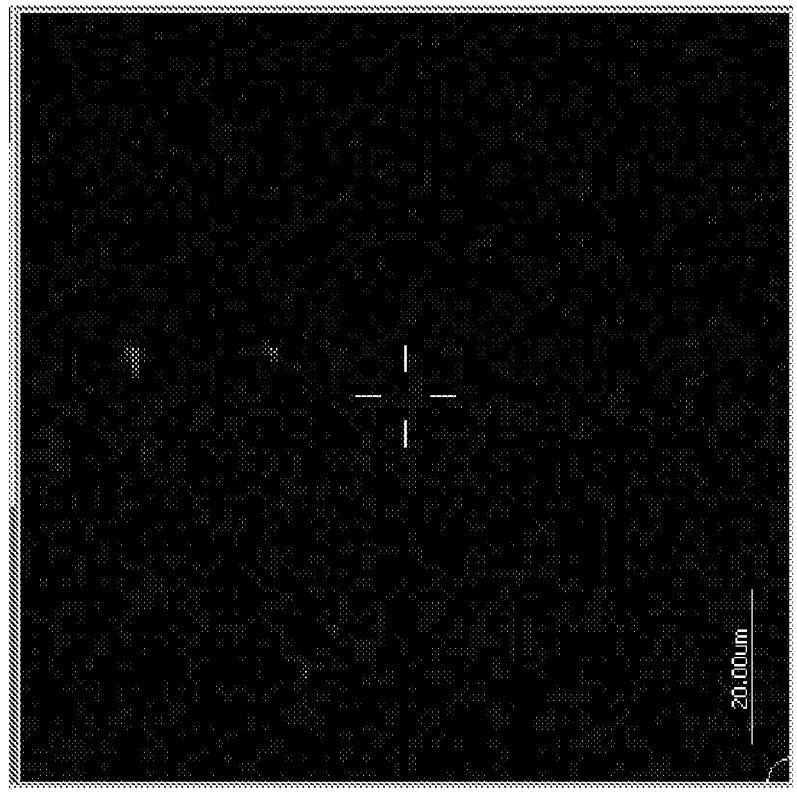
FIGS. 12A and 12B are photographs showing fused silica treated with $TaPEG_{550}$ then $PEG_{350}$-triphosphate before (FIG. 14A) and after (FIG. 14B) incubuation in DNA extension buffer wherein the slides were incubated with 100 nM LIZ-dATP and then rinsed with water to remove any unstuck dye.
Figure 12A:
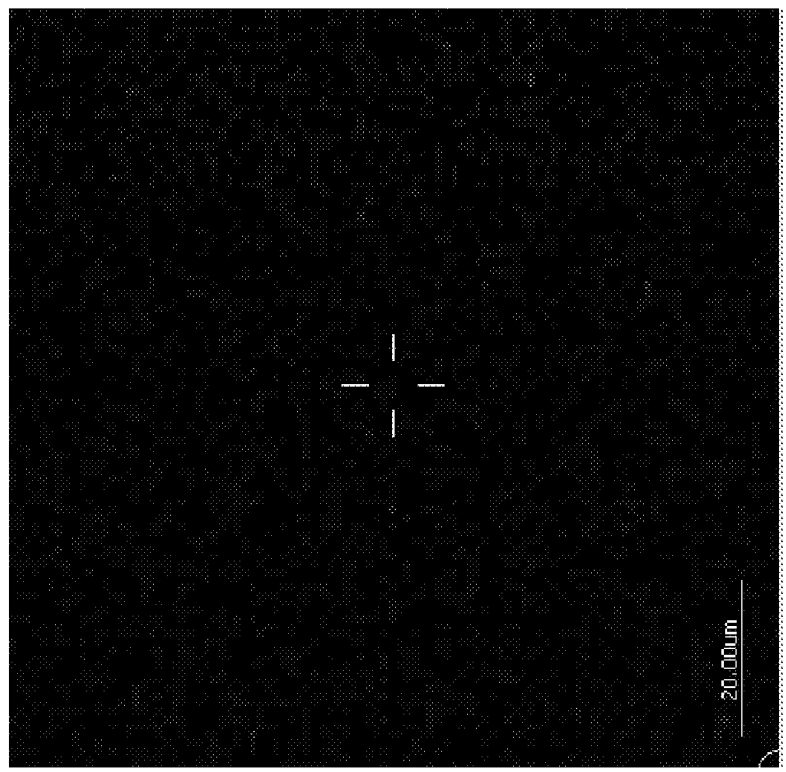

FIGS. 12A and 12B show fused silica surfaces treated with TaPEG$_{550}$ then PEG$_{350}$-triphosphate before (FIG. 12A) and after (FIG. 12B) incubation in DNA extension buffer. The PEG$_{350}$-triphosphate has a chemical structure as set forth below:

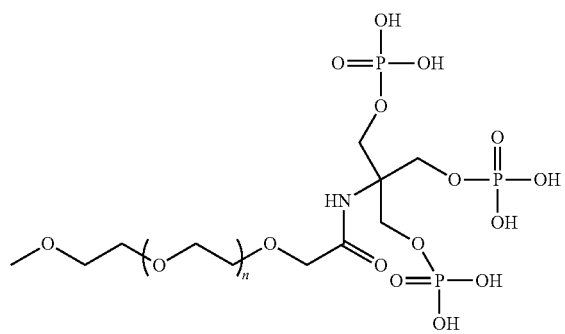

wherein n has a value such that the polyethylene glycol moiety has an average molecular weight of about 350. The treated surfaces were incubated with 100 nM LIZ-dATP and then rinsed with water to remove any dye that was not stuck to the surface. As can be seen from FIG. 12B, 100 nM LIZ-dATP exhibits minimal sticking to the modified surface even after the treated slide has been incubated with DNA extension buffer.

While the foregoing specification teaches the principles of the present invention, with examples provided for the purpose of illustration, it will be appreciated by one skilled in the art from reading this disclosure that various changes in form and detail can be made without departing from the true scope of the invention.

What is claimed is:

1. A method of modifying a surface of an oxide support material, the method comprising:
   providing an oxide support material having a surface with hydroxyl and/or oxide anion groups;
   contacting the hydroxyl and/or oxide anion groups of the surface of the oxide support material with a metal reagent; and
   allowing at least a portion of the metal reagent to react with at least a portion of the hydroxyl and/or oxide anion groups on the surface to form a modified surface for use in a bio-molecule detection scheme;
   wherein the metal reagent has a structure represented by the formula:

Y(L-Pol)$_m$ wherein:
   Y is a transition metal, magnesium or aluminum,
   L is oxygen, sulfur, selenium or an amine,
   each "Pol" group independently represents a polyethylene glycol, a substituted polyethylene glycol, a hydrocarbon, a substituted hydrocarbon, a fluorocarbon or a substituted fluorocarbon, and
   m is an integer.

2. The method of claim 1, further comprising:
   contacting the modified surface with a passivating composition comprising a compound of the formula (I), formula (II), or formula (III) below:

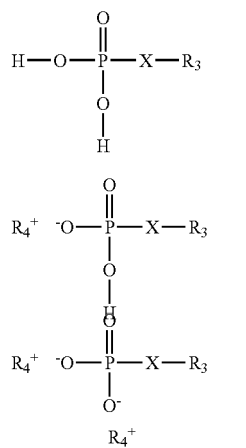

wherein:
   X is O, N or a methylene group;
   R$_3$ is polyethylene glycol, a substituted polyethylene glycol, a hydrocarbon, a substituted hydrocarbon, a fluorocarbon or a substituted fluorocarbon; and
   R$_4$ is N(R$_2$)$_4$, or M, wherein M is Li, Na, K or Cs and wherein R$_2$ is an alkyl group.

3. The method of claim 2, wherein the passivating composition comprises a compound of the formula (II) or a compound of the formula (III).

4. The method of claim 3, wherein R$_4$ is N(R$_2$)$_4$ wherein R$_2$ is an alkyl group.

5. The method of claim 1, further comprising pre-treating the surface of the support prior to contacting the surface of the support with the metal reagent, wherein pre-treating comprises treating the surface of the support with an oxygen plasma or contacting the surface of the support with tetrabutylammonium hydroxide, potassium hydroxide in methanol, hydrogen peroxide in sulfuric acid, nitric acid in sulfuric acid, hydrogen peroxide in ammonia, sulfuric acid, hydrofluoric acid, EDTA, or combinations thereof.

6. The method of claim 5, wherein the surface of the support is contacted with a base and wherein the base is tetrabutyl ammonium hydroxide.

7. The method of claim 1, wherein the support comprises an oxide of silicon, aluminum, germanium, gallium, indium, magnesium or tin.

8. The method of claim 1, wherein at least one "Pol" group is a polyethylene glycol or a substituted polyethylene glycol.

9. The method of claim 8, wherein at least one "Pol" group is a polyethylene glycol comprising biotin moieties.

10. The method of claim 2, wherein the passivating composition comprises a first phosphate compound of the formula (I), (II), or (III) having a first R$_3$ group and a second phosphate compound of the formula (I), (II), or (III) having a second R$_3$ group and wherein the first R$_3$ group is different than the second R$_3$ group.

11. The method of claim 2, wherein R$_3$ is a polyethylene glycol or a substituted polyethylene glycol.

12. The method of claim 1, further comprising:
    contacting the modified surface with a passivating composition comprising a metal complexing agent conjugated to a passivating agent, wherein:
    the metal complexing agent is selected from the group consisting of a carboxylate, dopamine and anachelin; and
    the passivating agent is selected from the group consisting of a polyethylene glycol, a substituted polyethylene glycol, a hydrocarbon, a substituted hydrocarbon, a fluorocarbon and a substituted fluorocarbon.

13. The method of claim 1, further comprising:
    contacting the modified surface with a polyvalent reagent comprising a passivating moiety and a plurality of functional groups that are reactive with Y or that form complexes with Y, wherein the passivating moiety is selected from the group consisting of a substituted polyethylene glycol, an unsubstituted polyethylene glycol, a hydrocarbon, a substituted hydrocarbon, a fluorocarbon and a substituted fluorocarbon.

14. The method of claim 13, wherein the plurality of functional groups that are reactive with Y or that form complexes with Y are selected from the group consisting of:
    hydroxyl groups, amine groups, phosphate groups, phosphonate groups, thiol groups, alkylphosphate groups, carboxyl groups and combinations thereof.

15. The method of claim 13, wherein the polyvalent reagent is represented by the following formula:

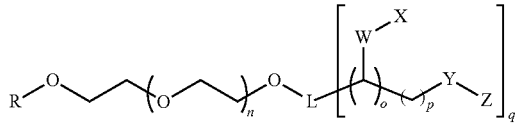

wherein:
R is H, alkyl, aryl or a functional group;
L is a linker group or a covalent bond;

each W and Y are independently O, NH, S or phosphonate;
each X and Z are independently H, phosphate, alkylcarboxy or alkylphosphate;
n is 3 to 100;
o is 1-8;
p is 0-8; and
q is 1-3.

16. The method of claim 15, wherein the linker L is represented by the formula: —(C)$_s$—(C=O)-Q-R'-Q-(C=O)— wherein each Q is independently —O— or —NH—, R' is an aliphatic or aromatic group and s is an integer of 0 to 10.

17. The method of claim 13, wherein the polyvalent reagent is represented by the following formula:

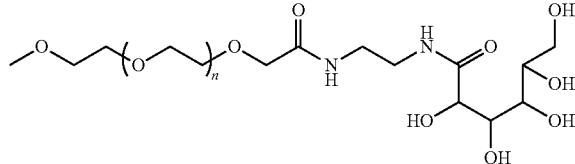

wherein n is a positive integer.

18. The method of claim 13, wherein the polyvalent reagent is represented by the following formula:

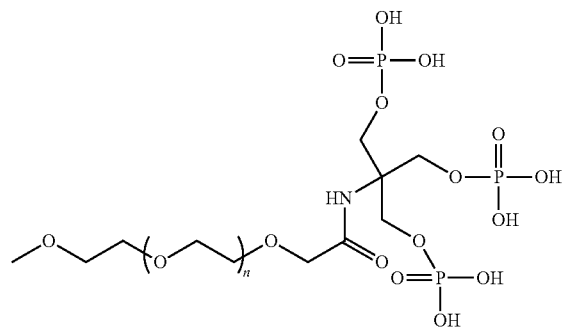

wherein n is a positive integer.

* * * * *